US007973062B2

(12) United States Patent
Chen et al.

(10) Patent No.: US 7,973,062 B2
(45) Date of Patent: *Jul. 5, 2011

(54) ANDROGEN RECEPTOR-ABLATIVE AGENTS

(75) Inventors: Ching-Shih Chen, Upper Arlington, OH (US); Dasheng Wang, Dublin, OH (US); Jian Yang, Columbus, OH (US)

(73) Assignee: The Ohio State University Research Foundation, Columbus, OH (US)

( * ) Notice: Subject to any disclaimer, the term of this patent is extended or adjusted under 35 U.S.C. 154(b) by 251 days.

This patent is subject to a terminal disclaimer.

(21) Appl. No.: 12/389,759

(22) Filed: Feb. 20, 2009

(65) Prior Publication Data

US 2009/0291992 A1 Nov. 26, 2009

Related U.S. Application Data

(60) Provisional application No. 61/030,860, filed on Feb. 22, 2008.

(51) Int. Cl.
*A61K 31/426* (2006.01)
*C07D 277/34* (2006.01)

(52) U.S. Cl. .................................... 514/369; 548/183
(58) Field of Classification Search .................. 548/183; 514/369
See application file for complete search history.

(56) References Cited

U.S. PATENT DOCUMENTS

| 4,376,777 | A | 3/1983 | Kawamatsu et al. | |
|---|---|---|---|---|
| 5,387,596 | A | 2/1995 | Takebayashi et al. | |
| 5,801,173 | A | 9/1998 | Lohray et al. | |
| 6,046,222 | A | 4/2000 | Atonucci et al. | |
| 6,765,013 | B2 | 7/2004 | Pfahl et al. | |
| 7,566,787 | B2 * | 7/2009 | Chen ........................... | 548/200 |
| 7,714,005 | B2 * | 5/2010 | Chen et al. ................... | 514/369 |
| 2006/0252801 | A1 | 11/2006 | Chen | |

FOREIGN PATENT DOCUMENTS

| EP | 454501 | 4/1991 |
|---|---|---|
| WO | 2006/069186 | 6/2006 |
| WO | 2006/069217 | 6/2006 |

OTHER PUBLICATIONS

Heinlein et al. Endocrine Reviews 2004, 25(2), 276-308.*
Schafer et al. Drug Discovery Today 2008, 13 (21/22), 913-916.*
Horig et al. Journal of Translational Medicine 2004, 2(44).*
Huang et al. J. Med. Chem. 2006, 49, 4684-4689.*
International Search Report and Written Opinion from PCT/US05/46454, mailed Jul. 14, 2006.
International Search Report and Written Opinion for PCT/US05/46534, mailed Mar. 14, 2008.
International Search Report and Written Opinion from PCT/US09/34650 dated Jul. 16, 2009.
Office action from U.S. Appl. No. 11/315,077 dated Jan. 2, 2009.
Amendment from U.S. Appl. No. 11/315,077 dated Mar. 30, 2009.
Office action from U.S. Appl. No. 11/315,569 dated May 19, 2008.
Amendment from U.S. Appl. No. 11/315,569 dated Nov. 19, 2008.
Notice of Allowance from U.S. Appl. No. 11/315,569 dated Mar. 24, 2009.
Altiok, et al., PPARgamma induces cell cycle withdrawal: inhibition of E2F/DP DNA-binding activity via down-regulation of PP2A. Genes Dev, 11: 1987-1998, 1997.
Cancer Topics [online], retrieved from the Internet Apr. 24, 2008, www.nci.nih.gov/cancertopics/druginfo/alphalist/pring?page=&keyword.
Clark et al., "Substituted dihydrobenzopyran and Dihydrobenzofuran Thiazolidine-2,4-diones as Hypoglycemic Agents", J Med Chem vol. 34, pp. 319-325, chart 1, 1991.
Golub et al., "Molecular Classification of Cancer: Class Discovery and Class Prediction by Gene Expression Monitoring", Science, vol. 286, pp. 531-537, Oct. 15, 1999.
Gupta, et al., Target genes of peroxisome proliferator-activated receptor gamma in colorectal cancer cells. J Biol Chem, 276: 29681-29687, 2001.
Huang et al (Jan. 13, 2005), Peroxisome Proliferator-Activated Receptor γ-Independent Ablation of Cyclin D1 by Thiazolidinediones and Their Derivatives in Breast Cancer Cells, Mol Pharmacol 67: 1342-1348.
Kwon, Handbook of Essential Pharmacokinetics, Pharmacodynamics and Drug Metabolism for Industrial Scientists, Jun. 24, 2001, Apr. 24, 2008.
Metabolomics [online], retrieved from the Internet Apr. 24, 2008, www.en.wikipedia.org/wiki/metabolomics.
Orlinskii, "Preparative synthesis method for thiazolidine-2, 4-dione and its N-derivatives", Pharmaceutical Chemical Journal, vol. 29, No. 2, pp. 144, 1995.
Palakurthi et al. (2001), Anticancer Effects of Thiazolidinediones are Independent of Peroxisome Proliferator-activated Receptor γ and Mediated by Inhibition of Translation Initiation, Cancer Res 61: 6213-6218.
Qin et al., (2003) Peroxisome proliferator-activated receptor gamma agonists induce proteasome-dependent degradation of cyclin D1 and estrogen receptor alpha in MCF-7 breast cancer cells. Cancer Res 63:958-64.
Reddy et al. (1999), Novel Antidiabetic and Hypolipedemic Agents. 5. Hydroxyl versus Benzyloxy Containing Chroman, Journal of Med Chem 42: 3265-3278.
Shiau et al. (Feb. 19, 2005), Thiazolidinediones Mediate Apoptosis in Prostate Cancer Cells in Part through Inhibition of Bcl-xL/Bcl-2 Functions Independently of PPARγ.
Tontonoz, et al., Terminal differentiation of human liposarcoma cells induced by ligands for peroxisome proliferator-activated receptor gamma and the retinoid X receptor. Proc Natl Acad Sci U S A, 94: 237-241, 1997.
Yang et al., "Peroxisome proliferator-activated receptor γ-Independent suppression of androgen receptor expression by troglitazone mechanism and pharmacologic exploitation", Cancer Res. 67(7), pp. 3229-3238 (2007).
Yang et al., "Pharmacological Exploitation of the Peroxisome Proliferator-Activated Receptor γ Agonist Ciglitazone to develop a novel class of Androgen Receptor-Ablative agents", J. Med Chem, 51, pp. 2100-2107 (2008).
Yu et al., (2001) Specific protection against breast cancers by cyclin D1 ablation. Nature 411:1017-21.

* cited by examiner

*Primary Examiner* — Jason M Nolan
(74) *Attorney, Agent, or Firm* — Calfee, Halter & Griswold LLP

(57) ABSTRACT

Compounds of the thiazolidinedione family are provided and shown to be effective androgen receptor ablative agents that can be used in methods of treating or preventing cancer or precancer, including prostate cancer. Also provided are methods of treating or preventing cancer by administering a therapeutically effective amount of one of the androgen receptor ablative agents to a subject in need of such treatment.

13 Claims, 6 Drawing Sheets

ANDROGEN RECEPTOR-ABLATIVE AGENTS

CONTINUING APPLICATION DATA

This application claims the benefit of U.S. Provisional Application Ser. No. 61/030,860, filed Feb. 22, 2008, which is incorporated by reference herein.

GOVERNMENT FUNDING

This invention was supported, at least in part, by National Institutes of Health Grants CA94829 and CA 112250, and Department of Defense Prostate Cancer Research Program Grant W81XWH-05-1-0089. The Federal Government may have certain rights in this invention.

BACKGROUND

The invention relates to androgen receptor-ablative agents and methods of using such agents for the treatment of cancer. Mounting evidence indicates that dysregulation of androgen receptor (AR) through gene amplification or mutations plays a key role in the development of androgen-refractory prostate cancer, a hallmark of incurable and lethal prostate cancer progression. These molecular changes enhance AR sensitivity or permit AR activation by antiestrogen, thus allowing prostate cancer cells to become resistant to androgen ablation-induced apoptosis. From a clinical perspective, targeting AR expression represents an important strategy to improve the treatment of androgen-independent prostate cancer and ultimately to increase the survival of prostate cancer patients.

A recent study indicates that knocking down the AR protein level by a small interfering RNA (siRNA) resulted in significant apoptotic cell death in LNCaP androgen-responsive prostate cancer cells, but not in the AR-null PC-3 cells. Moreover, in a LNCaP tumor xenograft model, short hairpin RNA (shRNA)-mediated AR knockdown was effective in blocking tumor growth and delaying tumor progression, which provides a proof-of-principle of this AR-targeted therapy. Studies have indicated that these AR-ablative agents mediate the transcriptional repression of androgen receptor through the downregulation of Sp1 expression. See Yang et al., Cancer Res., 67(7), p. 3229-3238 (2007). Since Sp1 has other target genes crucial to cancer cell survival, these agents could also suppress AR-independent cancer cell proliferation, and therefore provide anticancer effects beyond prostate cancer.

Although a number of natural product-based, small-molecule agents exhibit the ability to suppress AR expression, including resveratrol, vitamin E succinate, genistein, and curcumin, their therapeutic use in humans is limited by the high therapeutic concentration required by their low potency. Thus, there is an urgent need to develop potent AR-ablative agents to allow new strategies for cancer treatment, and in particular prostate cancer treatment.

SUMMARY OF THE INVENTION

The invention provides androgen receptor ablative agents that can be used in the treatment of cancers, and particularly prostate cancer. The androgen receptor ablative agents are thiazolidinedione compounds as defined by Formula's I-VII provided herein. Also provided are methods of treating cancer, the method including administering a therapeutically effective amount of one of the androgen receptor ablative agents described herein to a subject in need of such treatment. In one embodiment, the cancer is prostate cancer, and the subject is a human subject.

BRIEF DESCRIPTION OF THE DRAWINGS

The present invention may be more readily understood by reference to the following drawings wherein.

DETAILED DESCRIPTION OF THE INVENTION

Figure 1:
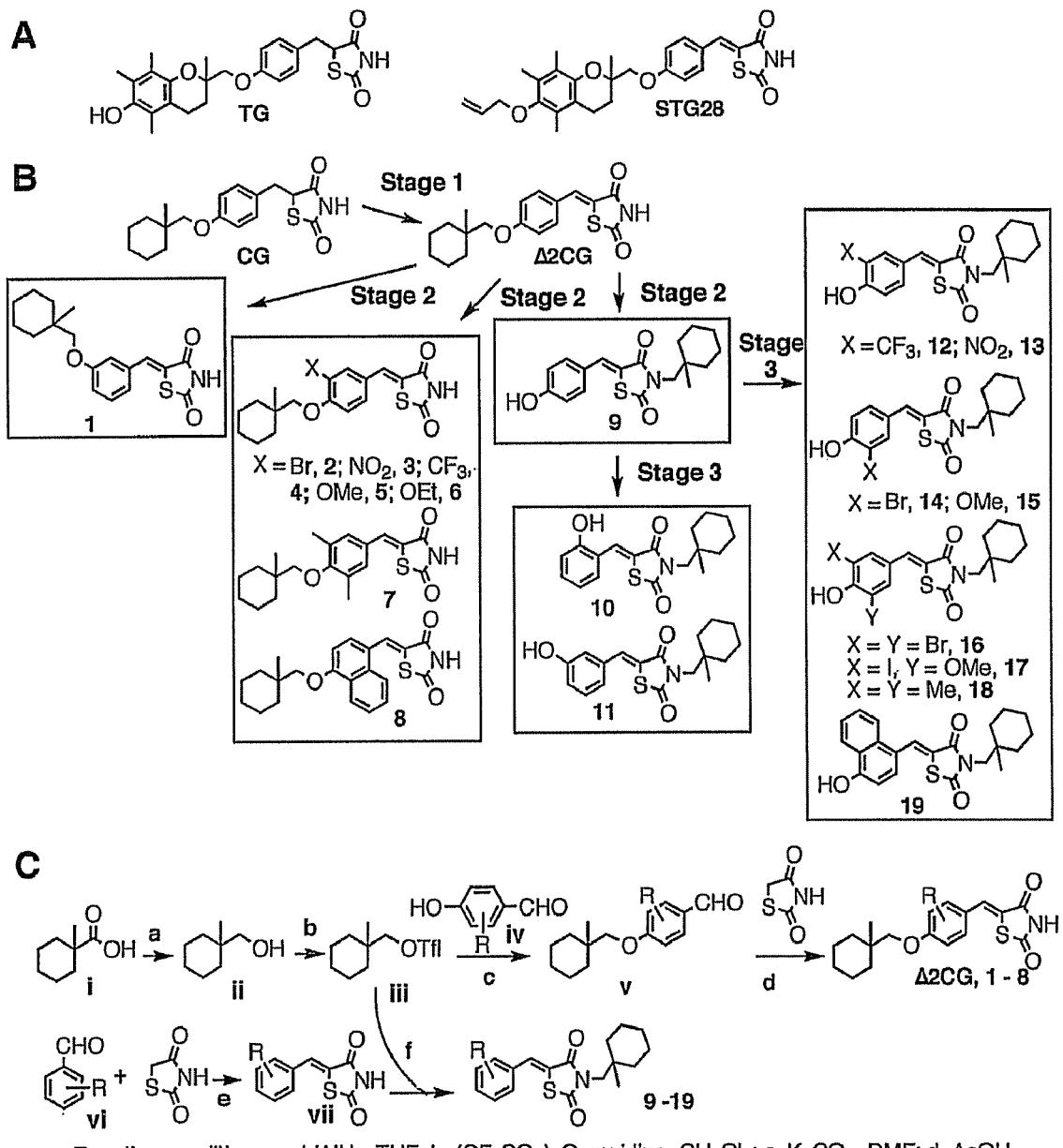
FIG. 1. (A) Shows representative structures of troglitazone (TG), STG28, ciglitazone (CG), and derivatives. (B) Shows a schematic representation of the course of structural optimization of ciglitazone to develop AR-ablative agents. (C) Shows the general synthetic procedure for ciglitazone derivatives.

Provided are new androgen receptor ablative agents useful in treating unwanted proliferating cells, including, but not limited to cancers and precancers. Some specific embodiments of the androgen receptor ablative agents are shown below. The ablative agents described herein further include derivatives, pharmaceutically acceptable salts, and metabolites thereof. Also provided are methods of using the androgen receptor ablative agents described herein in the treatment of unwanted proliferating cells in a subject, the method comprising administering a therapeutically effective amount of an androgen receptor ablative agent described herein to a subject in need of such treatment. In one embodiment, the method is a method of treating cancer in a subject comprising the step of administering a therapeutically effective amount of a androgen receptor ablative agent described herein to a subject having cancer.

In one embodiment, the method comprises a method of treating prostate cancer in a subject comprising the step of administering a therapeutically effective amount of an androgen receptor ablative agent described herein to a subject having prostate. Also provided are methods of preventing the proliferation of unwanted proliferating cells in a subject, the method comprising the step of administering a therapeutically effective amount of an androgen receptor ablative agent described herein to a subject at risk of developing a condition characterized by unwanted proliferation cells. In one embodiment, the method is a method of preventing cancer. In another embodiment, the method is a method of preventing prostate cancer. In some embodiments, the methods treating unwanted proliferating cells, including cancers and precancers, comprise inducing apoptosis in the unwanted proliferating cells by administering an effective amount of the androgen receptor ablative agent to the subject in need of such treatment.

In one embodiment, the invention provides a method of treating, inhibiting, or delaying the onset of a cancer in a subject in need of treatment, the method comprising administering a therapeutically effective amount of a compound of Formula I:

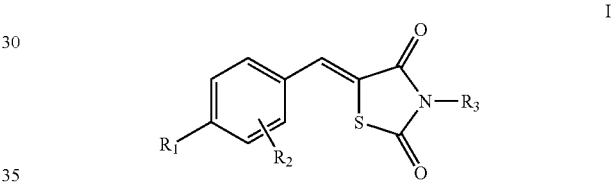

I wherein $R_1$ is selected from the group consisting of hydroxyl, amino, halo, hydroxyalkyl, alkylmethoxy, cycloalkylmethoxy, arylmethoxy, NHCOR, NHSO$_2$R, and CH$_2$R; wherein $R_2$ is selected from the group consisting of hydrogen, halo, amino, methoxy, ethoxy, nitro, phenyl, di-alkyl, di-halo, trifluoromethyl, and hydroxyl; and wherein $R_3$ is selected from the group consisting of hydrogen, alkyl, cyclic alkyl, and arylmethoxy; or a pharmaceutically-acceptable salt thereof, to the subject in need of such treatment.

In additional embodiments of the method of treating, inhibiting, or delaying the onset of a cancer using compounds of Formula I, the cancer may include leukemia, non-small cell lung cancer, colon cancer, CNS cancer, melanoma, ovarian cancer, renal cancer, prostate cancer, bladder cancer, lymphoma, or breast cancer. In further embodiments, the method is specifically directed to the treatment of prostate cancer, or hormone-refractory prostate cancer (HRPC).

In another embodiment of the invention, the androgen receptor ablative agents described herein have the structure shown in Formula I:

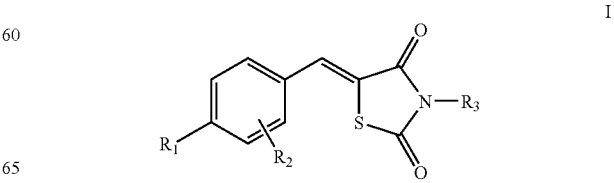

I wherein $R_1$ is selected from the group consisting of hydroxyl, amino, halo, hydroxyalkyl, alkylmethoxy, cycloalkylmethoxy, arylmethoxy, NHCOR, NHSO$_2$R, and CH$_2$R; wherein $R_2$ is selected from the group consisting of hydrogen, halo, amino, methoxy, ethoxy, nitro, phenyl, di-alkyl, di-halo, trifluoromethyl, and hydroxyl; and wherein $R_3$ is selected from the group consisting of hydrogen, alkyl, cyclic alkyl, and arylmethoxy.

Embodiments of the androgen receptor ablative agent of formula I include:
a. 5-[3-(1-Methyl-cyclohexylmethoxy)-benzylidene]-thiazolidine-2,4-dione;
b. 5-(2-Hydroxy-benzylidene)-3-(1-methyl-cyclohexylmethyl)-thiazolidine-2,4-dione; and
c. 5-(3-Hydroxy-benzylidene)-3-(1-methyl-cyclohexylmethyl)-thiazolidine-2,4-dione In a further embodiment of formula I, the androgen receptor ablative agent is

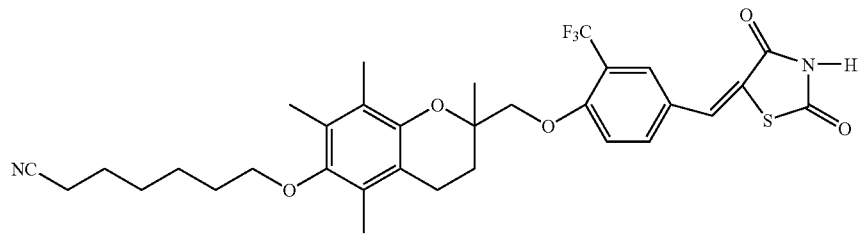

In another embodiment, the androgen receptor ablative agents described herein have the structure shown in Formula II:

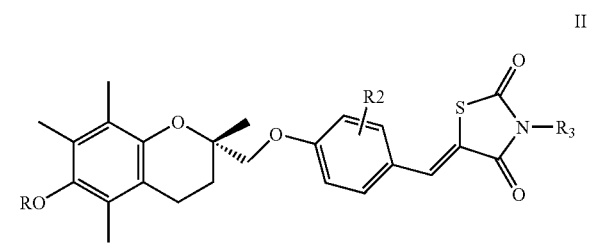

II wherein R is selected from the group consisting of hydrogen, alkyl, allyl, nitrile, ester, carbonyl, amide, and aryl; wherein $R_2$ is selected from the group consisting of hydrogen, halo, amino, methoxy, ethoxy, nitro, phenyl, di-alkyl, di-halo, trifluoromethyl, and hydroxyl; and wherein $R_3$ is selected from the group consisting of hydrogen, alkyl, cyclic alkyl, and arylmethoxy.

Embodiments of the androgen receptors of formula II include 5-[3-Bromo-4-(6-methoxy-2,5,7,8-tetramethyl-chroman-2-ylmethoxy)-benzylidene]-thiazolidine-2,4-dione; 5-[3-Bromo-4-(6-ethoxy-2,5,7,8-tetramethyl-chroman-2-ylmethoxy)-benzylidene]-thiazolidine-2,4-dione; 5-[3-Bromo-4-(2,5,7,8-tetramethyl-6-propoxy-chroman-2-ylmethoxy)-benzylidene]-thiazolidine-2,4-dione; 5-[3-Bromo-4-(6-butoxy-2,7,8-trimethyl-1,2,3,4-tetrahydro-naphthalen-2-ylmethoxy)-benzylidene]-thiazolidine-2,4-dione; 5-[3-Bromo-4-(2,5,7,8-tetramethyl-6-pentyloxy-chroman-2-ylmethoxy)-benzylidene]-thiazolidine-2,4-dione; 5-[3-Bromo-4-(6-hexyloxy-2,5,7,8-tetramethyl-chroman-2-ylmethoxy)-benzylidene]-thiazolidine-2,4-dione; 5-[3-Bromo-4-(6-heptyloxy-2,5,7,8-tetramethyl-chroman-2-ylmethoxy)-benzylidene]-thiazolidine-2,4-dione; 5-[3-Bromo-4-(6-isopropoxy-2,5,7,8-tetramethyl-chroman-2-ylmethoxy)-benzylidene]-thiazolidine-2,4-dione; 5-[3-Bromo-4-(6-sec-butoxy-2,5,7,8-tetramethyl-chroman-2-ylmethoxy)-benzylidene]-thiazolidine-2,4-dione; 5-[3-Bromo-4-(6-isobutoxy-2,5,7,8-tetramethyl-chroman-2-ylmethoxy)-benzylidene]-thiazolidine-2,4-dione; 5-{3-Bromo-4-[2,5,7,8-tetramethyl-6-(3-methyl-butoxy)-chroman-2-ylmethoxy]-benzylidene}-thiazolidine-2,4-dione; 5-{3-Bromo-4-[2,5,7,8-tetramethyl-6-(4-methyl-pentyloxy)-chroman-2-ylmethoxy]-benzylidene}-thiazolidine-2,4-dione; 5-[3-Bromo-4-(6-but-2-enyloxy-2,5,7,8-tetramethyl-chroman-2-ylmethoxy)-benzylidene]-thiazolidine-2,4-dione; 5-[3-Bromo-4-(2,5,7,8-tetramethyl-6-pent-2-enyloxy-chroman-2-ylmethoxy)-benzylidene]-thiazolidine-2,4-dione; 5-[4-(6-Allyloxy-2,5,7,8-tetramethyl-chroman-2-ylmethoxy)-3-trifluoromethyl-benzylidene]-thiazolidine-2,4-dione; 5-[4-(6-Butoxy-2,5,7,8-tetramethyl-chroman-2-ylmethoxy)-3-trifluoromethyl-benzylidene]-thiazolidine-2,4-dione; 5-[4-(2,5,7,8-Tetramethyl-6-pentyloxy-chroman-2-ylmethoxy)-3-trifluoromethyl-benzylidene]-thiazolidine-2,4-dione; 5-[4-(6-Hexyloxy-2,5,7,8-tetramethyl-chroman-2-ylmethoxy)-3-trifluoromethyl-benzylidene]-thiazolidine-2,4-dione; {2-[2-Bromo-4-(2,4-dioxo-thiazolidin-5-ylidenemethyl)-phenoxymethyl]-2,5,7,8-tetramethyl-chroman-6-yloxy}-acetonitrile; 3-{2-[2-Bromo-4-(2,4-dioxo-thiazolidin-5-ylidenemethyl)-phenoxymethyl]-2,5,7,8-tetramethyl-chroman-6-yloxy}-propionitrile; 4-{2-[2-Bromo-4-(2,4-dioxo-thiazolidin-5-ylidenemethyl)-phenoxymethyl]-2,5,7,8-tetramethyl-chroman-6-yloxy}-butyronitrile; 6-{2-[2-Bromo-4-(2,4-dioxo-thiazolidin-5-ylidenemethyl)-phenoxymethyl]-2,5,7,8-tetramethyl-chroman-6-yloxy}-hexanenitrile; 7-{6-[2-Bromo-4-(2,4-dioxo-thiazolidin-5-ylidenemethyl)-phenoxymethyl]-1,3,4,6-tetramethyl-5,6,7,8-tetrahydro-naphthalen-2-yloxy}-heptanenitrile; 6-{2-[2-Bromo-4-(2,4-dioxo-thiazolidin-5-ylidenemethyl)-phenoxymethyl]-2,5,7,8-tetramethyl-chroman-6-yloxy}-2,2-dimethyl-hexanenitrile; 4-{2-[4-(2,4-Dioxo-thiazolidin-5-ylidenemethyl)-2-trifluoromethyl-phenoxymethyl]-2,5,7,8-tetramethyl-chroman-6-yloxy}-butyronitrile; 6-{2-[4-(2,4-Dioxo-thiazolidin-5-ylidenemethyl)-2-trifluoromethyl-phenoxymethyl]-2,5,7,8-tetramethyl-chroman-6-yloxy}-hexanenitrile; 6-{2-[4-(2,4-Dioxo-thiazolidin-5-ylidenemethyl)-2-trifluoromethyl-phenoxymethyl]-2,5,7,8-tetramethyl-chroman-6-yloxy}-2,2-dimethyl-hexanenitrile; 7-{6-[4-(2,4-Dioxo-thiazolidin-5-ylidenemethyl)-2-trifluoromethyl-phenoxymethyl]-1,3,4,6-tetramethyl-5,6,7,8-tetrahydro-naphthalen-2-yloxy}-heptanenitrile; 4-{6-[4-(2,4-Dioxo-thiazolidin-5-ylidenemethyl)-2-trifluoromethyl-phenoxymethyl]-1,3,4,6-tetramethyl-5,6,7,8-tetrahydro-naphthalen-2-yloxymethyl}-benzonitrile; 5-[4-(6-Butoxy-2,5,7,8-tetramethyl-chroman-2-ylmethoxy)-3-methoxy-benzylidene]-thiazolidine-2,4-dione; 7-{2-[4-(2,4-Dioxothiazolidin-5-ylidenemethyl)-2-methoxy-phenoxymethyl]-2,5,7,8-tetramethyl-chroman-6-yloxy}-heptanenitrile; 5-{2-[2-Bromo-4-(2,4-dioxo-thiazolidin-5-ylidenemethyl)-phenoxymethyl]-2,5,7,8-tetramethyl-chroman-6-yloxy}-pentanoic acid methyl ester; 5-{6-[2-Bromo-4-(2,4-dioxo-thiazolidin-5-ylidenemethyl)-phenoxymethyl]-1,3,4,6-tetramethyl-5,6,7,8-tetrahydro-naphthalen-2-yloxy}-pentanoic acid ethyl ester; 5-{2-[4-(2,4-Dioxo-thiazolidin-5-ylidenemethyl)-2-trifluoromethyl-phenoxymethyl]-2,5,7,8-tetramethyl-chroman-6-yloxy}-pentanoic acid methyl ester; 5-{2-[4-(2,4-Dioxo-thiazolidin-5-ylidenemethyl)-2-trifluoromethyl-phenoxymethyl]-2,5,7,8-tetramethyl-chroman-6-yloxy}-pentanoic acid ethyl ester; 6-{2-[2-Bromo-4-(2,4-dioxo-thiazolidin-5-ylidenemethyl)-phenoxymethyl]-2,5,7,8-tetramethyl-chroman-6-yloxy}-hexanoic acid ethyl ester; 7-{2-[2-Bromo-4-(2,4-dioxo-thiazolidin-5-ylidenemethyl)-phenoxymethyl]-2,5,7,8-tetramethyl-chroman-6-yloxy}-heptanoic acid amide; 4-{2-[4-(2,4-Dioxo-thiazolidin-5-ylidenemethyl)-2-trifluoromethyl-phenoxymethyl]-2,5,7,8-tetramethyl-chroman-6-yloxy}-butyric acid ethyl ester; 5-[3-Bromo-4-(6-butoxy-2,5,7,8-tetramethyl-chroman-2-ylmethoxy)-benzylidene]-thiazolidine-2,4-dione; 4-{2-[4-(2,4-Dioxo-thiazolidin-5-ylidenemethyl)-2-trifluoromethyl-phenoxymethyl]-2,5,7,8-tetramethyl-chroman-6-yloxymethyl}-benzonitrile; and 5-[4-(6-Butoxy-2,5,7,8-tetramethyl-chroman-2-ylmethoxy)-3-methoxy-benzylidene]-thiazolidine-2,4-dione.

In further embodiments of the androgen receptor ablative agents of formula II, the embodiments include: a. 5-[3-Bromo-4-(6-methoxy-2,5,7,8-tetramethyl-chroman-2-ylmethoxy)-benzylidene]-thiazolidine-2,4-dione; b. 5-[3-Bromo-4-(6-ethoxy-2,5,7,8-tetramethyl-chroman-2-ylmethoxy)-benzylidene]-thiazolidine-2,4-dione; c. 5-[3-Bromo-4-(2,5,7,8-tetramethyl-6-propoxy-chroman-2-ylmethoxy)-benzylidene]-thiazolidine-2,4-dione; d. 5-[3-Bromo-4-(6-butoxy-2,5,7,8-tetramethyl-chroman-2-ylmethoxy)-benzylidene]-thiazolidine-2,4-dione; e. 4-{2-[4-(2,4-Dioxo-thiazolidin-5-ylidenemethyl)-2-trifluoromethyl-phenoxymethyl]-2,5,7,8-tetramethyl-chroman-6-yloxymethyl}-benzonitrile; f. 5-[4-(6-Butoxy-2,5,7,8-tetramethyl-chroman-2-ylmethoxy)-3-methoxy-benzylidene]-thiazolidine-2,4-dione; g. 7-{2-[4-(2,4-Dioxo-thiazolidin-5-ylidenemethyl)-2-methoxy-phenoxymethyl]-2,5,7,8-tetramethyl-chroman-6-yloxy}-heptanenitrile; h. 5-{2-[2-Bromo-4-(2,4-dioxo-thiazolidin-5-ylidenemethyl)-phenoxymethyl]-2,5,7,8-tetramethyl-chroman-6-yloxy}-pentanoic acid methyl ester; i. 5-{6-[2-Bromo-4-(2,4-dioxo-thiazolidin-5-ylidenemethyl)-phenoxymethyl]-1,3,4,6-tetramethyl-5,6,7,8-tetrahydro-naphthalen-2-yloxy}-pentanoic acid ethyl ester; j. 5-{2-[4-(2,4-Dioxo-thiazolidin-5-ylidenemethyl)-2-trifluoromethyl-phenoxymethyl]-2,5,7,8-tetramethyl-chroman-6-yloxy}-pentanoic acid methyl ester; k. 5-{2-[4-(2,4-Dioxo-thiazolidin-5-ylidenemethyl)-2-trifluoromethyl-phenoxymethyl]-2,5,7,8-tetramethyl-chroman-6-yloxy}-pentanoic acid ethyl ester; l. 6-{2-[2-Bromo-4-(2,4-dioxo-thiazolidin-5-ylidenemethyl)-phenoxymethyl]-2,5,7,8-tetramethyl-chroman-6-yloxy}-hexanoic acid ethyl ester; m. 7-{2-[2-Bromo-4-(2,4-dioxo-thiazolidin-5-ylidenemethyl)-phenoxymethyl]-2,5,7,8-tetramethyl-chroman-6-yloxy}-heptanoic acid amide; and n. 4-{2-[4-(2,4-Dioxo-thiazolidin-5-ylidenemethyl)-2-trifluoromethyl-phenoxymethyl]-2,5,7,8-tetramethyl-chroman-6-yloxy}-butyric acid ethyl ester.

In another embodiment, the androgen receptor ablative agents described herein have the structure shown in Formula III:

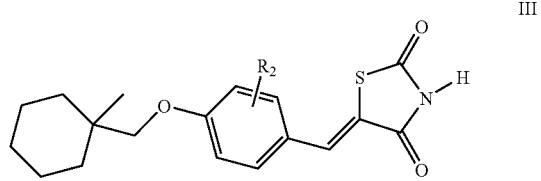

wherein $R_2$ is selected from the group consisting of hydrogen, halo, amino, methoxy, ethoxy, nitro, phenyl, di-alkyl, di-halo, trifluoromethyl, and hydroxyl.

In further embodiments of the androgen receptor ablative agents of formula III, the embodiments include: a. 5-[3-Bromo-4-(1-methyl-cyclohexylmethoxy)-benzylidene]-thiazolidine-2,4-dione; b. 5-[4-(1-Methyl-cyclohexylmethoxy)-3-nitro-benzylidene]-thiazolidine-2,4-dione; c. 5-[4-(1-Methyl-cyclohexylmethoxy)-3-trifluoromethyl-benzylidene]-thiazolidine-2,4-dione; d. 5-[3-Methoxy-4-(1-methyl-cyclohexylmethoxy)-benzylidene]-thiazolidine-2,4-dione; e. 5-[3-Ethoxy-4-(1-methyl-cyclohexylmethoxy)-benzylidene]-thiazolidine-2,4-dione; f. 5-[3,5-Dimethyl-4-(1-methyl-cyclohexylmethoxy)-benzylidene]-thiazolidine-2,4-dione; and g. 5-[4-(1-Methyl-cyclohexylmethoxy)-naphthalen-1-ylmethylene]-thiazolidine-2,4-dione;

In another embodiment, the androgen receptor ablative agents described herein have the structure shown in Formula IV:

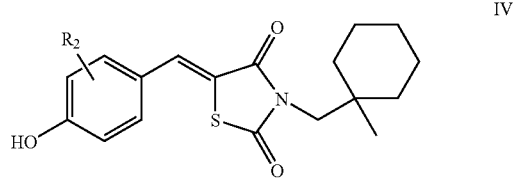

wherein $R_2$ is selected from the group consisting of hydrogen, halo, amino, methoxy, ethoxy, nitro, phenyl, di-alkyl, di-halo, trifluoromethyl, and hydroxyl.

In further embodiments of the androgen receptor ablative agents of formula IV, the embodiments include: a. 5-(4-Hydroxy-benzylidene)-3-(1-methyl-cyclohexylmethyl)-thiazolidine-2,4-dione; b. 5-(4-Hydroxy-3-trifluoromethyl-benzylidene)-3-(1-methyl-cyclohexylmethyl)-thiazolidine-2,4-dione; c. 5-(4-Hydroxy-3-nitro-benzylidene)-3-(1-methyl-cyclohexylmethyl)-thiazolidine-2,4-dione; d. 5-(3-Bromo-4-hydroxy-benzylidene)-3-(1-methyl-cyclohexylmethyl)-thiazolidine-2,4-dione; e. 5-(4-Hydroxy-3-methoxy-benzylidene)-3-(1-methyl-cyclohexylmethyl)-thiazolidine-2,4-dione; f. 5-(3,5-Dibromo-4-hydroxy-benzylidene)-3-(1-methyl-cyclohexylmethyl)-thiazolidine-2,4-dione; g. 5-(4-Hydroxy-3-iodo-5-methoxy-benzylidene)-3-(1-methyl-cyclohexylmethyl)-thiazolidine-2,4-dione; h. 5-(4-Hydroxy-3,5-dimethyl-benzylidene)-3-(1-methyl-cyclohexylmethyl)-thiazolidine-2,4-dione; and i. 5-(4-Hydroxy-naphthalen-1-ylmethylene)-3-(1-methyl-cyclohexylmethyl)-thiazolidine-2,4-dione;

In another embodiment, the androgen receptor ablative agents described herein have the structure shown in Formula V:

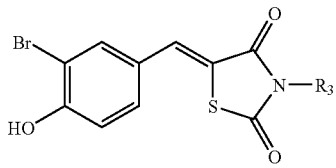

V wherein R₃ is selected from the group consisting of hydrogen, alkyl, cyclic alkyl, and arylmethoxy.

In further embodiments of the androgen receptor ablative agents of formula V, the embodiments include: a. 5-(3-Bromo-4-hydroxy-benzylidene)-3-ethyl-thiazolidine-2,4-dione; b. 5-(3-Bromo-4-hydroxy-benzylidene)-3-propyl-thiazolidine-2,4-dione; c. 5-(3-Bromo-4-hydroxy-benzylidene)-3-butyl-thiazolidine-2,4-dione; d. 5-(3-Bromo-4-hydroxy-benzylidene)-3-pentyl-thiazolidine-2,4-dione; e. 5-(3-Bromo-4-hydroxy-benzylidene)-3-isopropyl-thiazolidine-2,4-dione; f. 5-(3-Bromo-4-hydroxy-benzylidene)-3-(4-methyl-pentyl)-thiazolidine-2,4-dione; g. 5-(3-Bromo-4-hydroxy-benzylidene)-3-cyclohexylmethyl-thiazolidine-2,4-dione; h. 3-Allyl-5-(3-bromo-4-hydroxy-benzylidene)-thiazolidine-2,4-dione; i. 5-(3-Bromo-4-hydroxy-benzylidene)-3-(3-methyl-but-2-enyl)-thiazolidine-2,4-dione; j. 3-Benzyl-5-(3-bromo-4-hydroxy-benzylidene)-thiazolidine-2,4-dione; k. 4-[5-(3-Bromo-4-hydroxy-benzylidene)-2,4-dioxo-thiazolidin-3-ylmethyl]-benzonitrile; l. 4-[5-(3-Bromo-4-hydroxy-benzylidene)-2,4-dioxo-thiazolidin-3-yl]-butyronitrile; m. 4-[5-(3-Bromo-4-hydroxy-benzylidene)-2,4-dioxo-thiazolidin-3-yl]-butyric acid ethyl ester; n. 6-[5-(3-Bromo-4-hydroxy-benzylidene)-2,4-dioxo-thiazolidin-3-yl]-2,2-dimethyl-hexanenitrile; o. 5-(3-Bromo-4-hydroxy-benzylidene)-3-(tetrahydro-pyran-2-ylmethyl)-thiazolidine-2,4-dione; p. 5-(3-Bromo-4-hydroxy-benzylidene)-3-(6,6-dimethyl-[1,3]dioxan-4-ylmethyl)-thiazolidine-2,4-dione; q. 5-(3-Bromo-4-hydroxy-benzylidene)-3-naphthalen-1-ylmethyl-thiazolidine-2,4-dione; r. 5-(3-Bromo-4-hydroxy-benzylidene)-3-(3-chloro-5-fluoro-benzyl)-thiazolidine-2,4-dione; s. 5-(3-Bromo-4-hydroxy-benzylidene)-3-(2,3-dihydro-benzo[1,4]dioxin-2-ylmethyl)-thiazolidine-2,4-dione; t. 3-(4-Benzoyl-benzyl)-5-(3-bromo-4-hydroxy-benzylidene)-thiazolidine-2,4-dione; and u. 4'-[5-(3-Bromo-4-hydroxy-benzylidene)-2,4-dioxo-thiazolidin-3-ylmethyl]-biphenyl-2-carbonitrile.

In another embodiment, the androgen receptor ablative agents described herein have the structure shown in Formula VI:

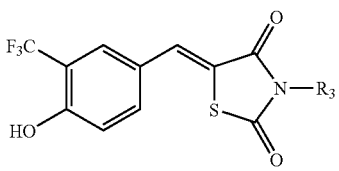

VI wherein R₃ is selected from the group consisting of hydrogen, alkyl, cyclic alkyl, and arylmethoxy.

In further embodiments of the androgen receptor ablative agents of formula VI, the embodiments include: a. 5-(3-Trifluoromethyl-4-hydroxy-benzylidene)-3-ethyl-thiazolidine-2,4-dione; b. 5-(3-Trifluoromethyl-4-hydroxy-benzylidene)-3-propyl-thiazolidine-2,4-dione; c. 5-(3-Trifluoromethyl-4-hydroxy-benzylidene)-3-butyl-thiazolidine-2,4-dione; d. 5-(3-Trifluoromethyl-4-hydroxy-benzylidene)-3-pentyl-thiazolidine-2,4-dione; e. 5-(3-Trifluoromethyl-4-hydroxy-benzylidene)-3-isopropyl-thiazolidine-2,4-dione; f. 5-(3-Trifluoromethyl-4-hydroxy-benzylidene)-3-(4-methyl-pentyl)-thiazolidine-2,4-dione; g. 5-(3-Trifluoromethyl-4-hydroxy-benzylidene)-3-cyclohexylmethyl-thiazolidine-2,4-dione; h. 3-Allyl-5-(3-Trifluoromethyl-4-hydroxy-benzylidene)-thiazolidine-2,4-dione; i. 5-(3-Trifluoromethyl-4-hydroxy-benzylidene)-3-(3-methyl-but-2-enyl)-thiazolidine-2,4-dione; j. 3-Benzyl-5-(3-Trifluoromethyl-4-hydroxy-benzylidene)-thiazolidine-2,4-dione; k. 4-[5-(3-Trifluoromethyl-4-hydroxy-benzylidene)-2,4-dioxo-thiazolidin-3-ylmethyl]-benzonitrile; l. 4-[5-(3-Trifluoromethyl-4-hydroxy-benzylidene)-2,4-dioxo-thiazolidin-3-yl]-butyronitrile; m. 4-[5-(3-Trifluoromethyl-4-hydroxy-benzylidene)-2,4-dioxo-thiazolidin-3-yl]-butyric acid ethyl ester; n. 6-[5-(3-Trifluoromethyl-4-hydroxy-benzylidene)-2,4-dioxo-thiazolidin-3-yl]-2,2-dimethyl-hexanenitrile; o. 5-(3-Trifluoromethyl-4-hydroxy-benzylidene)-3-(tetrahydro-pyran-2-ylmethyl)-thiazolidine-2,4-dione; p. 5-(3-Trifluoromethyl-4-hydroxy-benzylidene)-3-(6,6-dimethyl-[1,3]dioxan-4-ylmethyl)-thiazolidine-2,4-dione; q. 5-(3-Trifluoromethyl-4-hydroxy-benzylidene)-3-naphthalen-1-ylmethyl-thiazolidine-2,4-dione; r. 5-(3-Trifluoromethyl-4-hydroxy-benzylidene)-3-(3-chloro-5-fluoro-benzyl)-thiazolidine-2,4-dione; s. 5-(3-Trifluoromethyl-4-hydroxy-benzylidene)-3-(2,3-dihydro-benzo[1,4]dioxin-2-ylmethyl)-thiazolidine-2,4-dione; t. 3-(4-Benzoyl-benzyl)-5-(3-Trifluoromethyl-4-hydroxy-benzylidene)-thiazolidine-2,4-dione; and u. 4'-[5-(3-Trifluoromethyl-4-hydroxy-benzylidene)-2,4-dioxo-thiazolidin-3-ylmethyl]-biphenyl-2-carbonitrile;

In another embodiment, the androgen receptor ablative agents described herein have the structure shown in Formula VII:

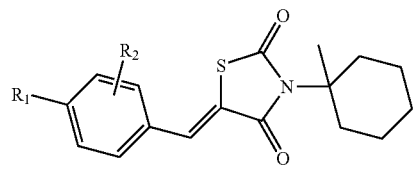

VII wherein R₁ is selected from the group consisting of hydroxyl, amino, halo, hydroxyalkyl, alkylmethoxy, cycloalkylmethoxy, arylmethoxy, NHCOR, NHSO₂R, and CH₂R;

wherein R₂ is selected from the group consisting of hydrogen, bromo, and trifluoromethyl;

In further embodiments of the androgen receptor ablative agents of formula VII, the embodiments include: a. 5-(4-Fluoro-benzylidene)-3-(1-methyl-cyclohexylmethyl)-thiazolidine-2,4-dione; b. 5-(4-Chloro-benzylidene)-3-(1-methyl-cyclohexylmethyl)-thiazolidine-2,4-dione; c. 5-(4-Bromo-benzylidene)-3-(1-methyl-cyclohexylmethyl)-thiazolidine-2,4-dione; d. 3-(1-Methyl-cyclohexylmethyl)-5-(4-nitro-benzylidene)-thiazolidine-2,4-dione; e. 3-(1-Methyl-cyclohexylmethyl)-5-(4-trifluoromethoxy-benzylidene)-thiazolidine-2,4-dione; f. 5-(4-Diethylamino-benzylidene)-3-(1-methyl-cyclohexylmethyl)-thiazolidine-2,4-dione; g. 5-(4-Dimethylamino-benzylidene)-3-(1- methyl-cyclohexylmethyl)-thiazolidine-2,4-dione; h. 5-(4-Hydroxymethyl-benzylidene)-3-(1-methyl-cyclohexylmethyl)-thiazolidine-2,4-dione; i. 4-[3-(1-Methyl-cyclohexylmethyl)-2,4-dioxo-thiazolidin-5-ylidenemethyl]-benzonitrile; j. 4-[3-(1-Methyl-cyclohexylmethyl)-2,4-dioxo-thiazolidin-5-ylidenemethyl]-benzaldehyde; k. 4-[3-(1-Methyl-cyclohexylmethyl)-2,4-dioxo-thiazolidin-5-ylidenemethyl]-benzoic acid methyl ester; l. 4-[3-(1-Methyl-cyclohexylmethyl)-2,4-dioxo-thiazolidin-5-ylidenemethyl]-benzoic acid; m. N-{4-[3-(1-Methyl-cyclohexylmethyl)-2,4-dioxo-thiazolidin-5-ylidenemethyl]-phenyl}-acetamide; n. N-{4-[3-(1-Methyl-cyclohexylmethyl)-2,4-dioxo-thiazolidin-5-ylidenemethyl]-phenyl}-propionamide; o. Hexadecanoic acid {4-[3-(1-methyl-cyclohexylmethyl)-2,4-dioxo-thiazolidin-5-ylidenemethyl]-phenyl}-amide; p. Cyclohexanecarboxylic acid {4-[3-(1-methyl-cyclohexylmethyl)-2,4-dioxo-thiazolidin-5-ylidenemethyl]-phenyl}-amide; q. 2,2,2-Trichloro-N-{4-[3-(1-methyl-cyclohexylmethyl)-2,4-dioxo-thiazolidin-5-ylidenemethyl]-phenyl}-acetamide; r. N-{4-[3-(1-Methyl-cyclohexylmethyl)-2,4-dioxo-thiazolidin-5-ylidenemethyl]-phenyl}-benzamide; s. N-{4-[3-(1-Methyl-cyclohexylmethyl)-2,4-dioxo-thiazolidin-5-ylidenemethyl]-phenyl}-methanesulfonamide; t. N-{4-[3-(1-Methyl-cyclohexylmethyl)-2,4-dioxo-thiazolidin-5-ylidenemethyl]-phenyl}-2-nitro-benzenesulfonamide; u. N-(4-{4-[3-(1-Methyl-cyclohexylmethyl)-2,4-dioxo-thiazolidin-5-ylidenemethyl]-phenylsulfamoyl}-phenyl)-acetamide; v. 4-Methyl-N-{4-[3-(1-methyl-cyclohexylmethyl)-2,4-dioxo-thiazolidin-5-ylidenemethyl]-phenyl}-benzenesulfonamide; w. 4-Chloro-N-{4-[3-(1-methyl-cyclohexylmethyl)-2,4-dioxo-thiazolidin-5-ylidenemethyl]-phenyl}-benzenesulfonamide; x. 4-(Z)-Acetyl-N-{4-[3-(1-methyl-cyclohexylmethyl)-2,4-dioxo-thiazolidin-5-ylidenemethyl]-phenyl}-benzenesulfonamide; y. N-{4-[3-(1-Methyl-cyclohexylmethyl)-2,4-dioxo-thiazolidin-5-ylidenemethyl]-phenyl}-4-nitro-benzenesulfonamide; z. N-{4-[3-(1-Methyl-cyclohexylmethyl)-2,4-dioxo-thiazolidin-5-ylidenemethyl]-phenyl}-4-nitro-3-trifluoromethyl-benzenesulfonamide; aa. 4-Chloro-N-{4-[3-(1-methyl-cyclohexylmethyl)-2,4-dioxo-thiazolidin-5-ylidenemethyl]-phenyl}-3-nitro-benzenesulfonamide; ab. 2-Methoxy-N-{4-[3-(1-methyl-cyclohexylmethyl)-2,4-dioxo-thiazolidin-5-ylidenemethyl]-phenyl}-4-nitro-benzenesulfonamide, and ac. 3,4-Dimethoxy-N-{4-[3-(1-methyl-cyclohexylmethyl)-2,4-dioxo-thiazolidin-5-ylidenemethyl]-phenyl}-benzenesulfonamide.

Further embodiments of the invention include derivatives and metabolites of the androgen receptor ablative agents of the formulas and compounds shown herein.

Prostate cancer, as used herein, refers to a disease in which cancer develops in the prostate gland of the male reproductive system. Prostate cancer is classified as an adenocarcinoma, or glandular cancer, that begins when normal semen-secreting prostate gland cells mutate into cancer cells. In the initial stage of prostate cancer, small clumps of cancer cells remain confined to otherwise normal prostate glands, a condition known as carcinoma in situ or prostatic intraepithelial neoplasia (PIN), a prostate precancer. Over time these cancer cells begin to multiply and spread to the surrounding prostate tissue (the stroma), forming a tumor. While prostate cancer originates and may remain in the prostate, prostate tumor cells may develop the ability to travel in the bloodstream and lymphatic system and thus be found in other organs or tissues. Prostate cancer most commonly metastasizes to the bones, lymph nodes, rectum, and bladder. Treatment or prevention of prostate cancer, as used herein, also refers to the treatment of metastasized prostate cancer found in other organs or tissues.

Sp1, as used herein, refers to a transcription factor that controls the expression of genes and the synthesis of other proteins that are important to certain aspects of tumor biology, including cell division, movement, resistance to therapy and the metastasis of cancer cells. Accordingly, the androgen receptor-ablative agents described herein are suitable for preventing or attenuating the growth of cancer cells characterized in part by excessive Sp1 expression.

Treat", "treating", and "treatment", etc., as used herein, refer to any action providing a benefit to a subject at risk for or afflicted with a disease, including improvement in the condition through lessening or suppression of at least one symptom, delay in progression of the disease, prevention or delay in the onset of the disease, etc. "Inhibit" as used herein refers to the partial or complete elimination of a potential effect, while inhibitors are compounds that have the ability to inhibit.

The terms "therapeutically effective" and "pharmacologically effective" are intended to qualify the amount of each agent which will achieve the goal of improvement in disease severity and the frequency of incidence over treatment of each agent by itself, while avoiding adverse side effects typically associated with alternative therapies. The effectiveness of treatment may be measured by evaluating a reduction in tumor load or decrease in tumor growth in a subject in response to the administration of androgen receptor-ablative agents. The reduction in tumor load may be represent a direct decrease in mass, or it may be measured in terms of tumor growth delay, which is calculated by subtracting the average time for control tumors to grow over to a certain volume from the time required for treated tumors to grow to the same volume.

As used herein, the term "prevention" includes either preventing the onset of a clinically evident unwanted cell proliferation altogether or preventing the onset of a preclinically evident stage of unwanted rapid cell proliferation in individuals at risk. Also intended to be encompassed by this definition is the prevention of metastasis of malignant cells or to arrest or reverse the progression of malignant cells. This includes prophylactic treatment of those at risk of developing precancers and cancers.

The term "subject" for purposes of treatment includes any human or animal subject who has a disorder characterized by unwanted, rapid cell proliferation. Such disorders include, but are not limited to cancers and precancers of the prostate. For methods of prevention the subject is any human or animal subject, and preferably is a human subject who is at risk of obtaining a disorder characterized by unwanted, rapid cell proliferation, such as cancer. The subject may be at risk due to exposure to carcinogenic agents, being genetically predisposed to disorders characterized by unwanted, rapid cell proliferation, and so on. Besides being useful for human treatment, the compounds of the present invention are also useful for veterinary treatment of mammals, including companion animals and farm animals, such as, but not limited to dogs, cats, horses, cows, sheep, and pigs. In most embodiments, subject means a human.

The phrase "pharmaceutically acceptable salts" connotes salts commonly used to form alkali metal salts and to form addition salts of free acids or free bases. The nature of the salt is not critical, provided that it is pharmaceutically acceptable. Suitable pharmaceutically acceptable acid addition salts of compounds of formulae I-VII may be prepared from an inorganic acid or from an organic acid. Examples of such inorganic acids are hydrochloric, hydrobromic, hydroiodic, nitric, carbonic, sulfuric, and phosphoric acid. Appropriate organic acids may be selected from aliphatic, cycloaliphatic, aromatic, araliphatic, heterocyclic, carboxylic, and sulfonic classes of organic acids, examples of which include formic, acetic, propionic, succinic, glycolic, gluconic, lactic, malic, tartaric, citric, ascorbic, glucoronic, maleic, fumaric, pyruvic, aspartic, glutamic, benzoic, anthranilic, mesylic, salicylic, p-hydroxybenzoic, phenylacetic, mandelic, ambonic, pamoic, methanesulfonic, ethanesulfonic, benzenesulfonic, pantothenic, 2-hydroxyethanesulfonic, toluenesulfonic, sulfanilic, cyclohexylaminosulfonic, stearic, algenic, β-hydroxybutyric, galactaric, and galacturonic acids. Suitable pharmaceutically acceptable base addition salts of the compounds described herein include metallic salts made from aluminum, cakium, lithium, magnesium, potassium, sodium, and zinc. Alternatively, organic salts made from N,N'-dibenzylethylenediamine, chloroprocaine, choline, diethanolamine, ethylenediamine, meglumine (N-methylglucamine) and procaine may be used form base addition salts of the compounds described herein. All of these salts may be prepared by conventional means from the corresponding compounds described herein by reacting, for example, the appropriate acid or base with the compound.

Where the term alkyl is used, either alone or with other terms, such as haloalkyl or alkylaryl, it includes $C_1$ to $C_{10}$ linear or branched alkyl radicals, examples include methyl, ethyl, propyl, isopropyl, butyl, tert-butyl, and so forth. The term "haloalkyl" includes $C_1$ to $C_{10}$ linear or branched alkyl radicals substituted with one or more halo radicals. Some examples of haloalkyl radicals include trifluoromethyl, 1,2-dichloroethyl, 3-bromopropyl, and so forth. The term "halo" includes radicals selected from F, Cl, Br, and I. Alkyl radical substituents of the present invention may also be substituted with other groups such as azido, for example, azidomethyl, 2-azidoethyl, 3-azidopropyl and so on.

The term aryl, used alone or in combination with other terms such as alkylaryl, haloaryl, or haloalkylaryl, includes such aromatic radicals as phenyl, biphenyl, and benzyl, as well as fused aryl radicals such as naphthyl, anthryl, phenanthrenyl, fluorenyl, and indenyl and so forth. The term "aryl" also encompasses "heteroaryls," which are aryls that have carbon and one or more heteroatoms, such as O, N, or S in the aromatic ring. Examples of heteroaryls include indolyl, pyrrolyl, and so on. "Alkylaryl" or "arylalkyl" refers to alkyl-substituted aryl groups such as butylphenyl, propylphenyl, ethylphenyl, methylphenyl, 3,5-dimethylphenyl, tert-butylphenyl and so forth. "Haloaryl" refers to aryl radicals in which one or more substitutable positions has been substituted with a halo radical, examples include fluorophenyl, 4-chlorophenyl, 2,5-chlorophenyl and so forth. "Haloalkylaryl" refers to aryl radicals that have a haloalkyl substituent.

Provided are pharmaceutical compositions for ablating androgen receptors in cells such as LNCaP cells. These compounds are also useful for treating, preventing, or delaying the onset of prostate cancer in a subject in need of such treatment. The pharmaceutical composition comprises a therapeutically effective amount of a compound disclosed herein, or a derivative or pharmaceutically acceptable salt thereof, in association with at least one pharmaceutically acceptable carrier, adjuvant, or diluent (collectively referred to herein as "carrier materials") and, if desired, other active ingredients. The active compounds of the present invention may be administered by any suitable route known to those skilled in the art, preferably in the form of a pharmaceutical composition adapted to such a route, and in a dose effective for the treatment intended. The active compounds and composition may, for example, be administered orally, intra-vascularly, intraperitoneally, intranasal, intrabronchial, subcutaneously, intramuscularly or topically (including aerosol). With some subjects local administration, rather than system administration, may be preferred. Formulation in a lipid vehicle may be used to enhance bioavailability.

The administration of the present invention may be for either prevention or treatment purposes. The methods and compositions used herein may be used alone or in conjunction with additional therapies known to those skilled in the art in the prevention or treatment of disorders characterized by unwanted, rapid proliferation of cells. Alternatively, the methods and compositions described herein may be used as adjunct therapy. By way of example, the compounds of the present invention may be administered alone or in conjunction with other antineoplastic agents or other growth inhibiting agents or other drugs or nutrients, as in an adjunct therapy.

The phrase "adjunct therapy" or "combination therapy" in defining use of a compound described herein and one or more other pharmaceutical agents, is intended to embrace administration of each agent in a sequential manner in a regimen that will provide beneficial effects of the drug combination, and is intended as well to embrace co-administration of these agents in a substantially simultaneous manner, such as in a single formulation having a fixed ratio of these active agents, or in multiple, separate formulations for each agent.

For the purposes of combination therapy, there are large numbers of antineoplastic agents available in commercial use, in clinical evaluation and in pre-clinical development, which could be selected for treatment of cancers or other disorders characterized by rapid proliferation of cells by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents. Alternatively, other anti-neoplastic agents, such as metallomatrix proteases inhibitors (MMP), such as MMP-13 inhibitors, or $\alpha_v\beta_3$ inhibitors may be used. Suitable agents which may be used in combination therapy will be recognized by those of skill in the art. Similarly, when combination with radiotherapy is desired, radioprotective agents known to those of skill in the art may also be used. Treatment using compounds of the present invention can also be combined with treatments such as hormonal therapy, proton therapy, cryosurgery, and high intensity focused ultrasound (HIFU), depending on the clinical scenario and desired outcome.

When preparing the compounds described herein for oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable carrier.

For intravenous, intramuscular, subcutaneous, or intraperitoneal administration, the compound may be combined with a sterile aqueous solution which is preferably isotonic with the blood of the recipient. Such formulations may be prepared by dissolving solid active ingredient in water containing physiologically compatible substances such as sodium chloride, glycine, and the like, and having a buffered pH compatible with physiological conditions to produce an aqueous solution, and rendering said solution sterile. The formulations may be present in unit or multi-dose containers such as sealed ampoules or vials.

Formulations suitable for parenteral administration conveniently comprise a sterile aqueous preparation of the active compound which is preferably made isotonic. Preparations for injections may also be formulated by suspending or emulsifying the compounds in non-aqueous solvent, such as vegetable oil, synthetic aliphatic acid glycerides, esters of higher aliphatic acids or propylene glycol.

The dosage form and amount can be readily established by reference to known treatment or prophylactic regiments. The amount of therapeutically active compound that is administered and the dosage regimen for treating a disease condition with the compounds and/or compositions of this invention depends on a variety of factors, including the age, weight, sex, and medical condition of the subject, the severity of the disease, the route and frequency of administration, and the particular compound employed, the location of the unwanted proliferating cells, as well as the pharmacokinetic properties of the individual treated, and thus may vary widely. The dosage will generally be lower if the compounds are administered locally rather than systemically, and for prevention rather than for treatment. Such treatments may be administered as often as necessary and for the period of time judged necessary by the treating physician. One of skill in the art will appreciate that the dosage regime or therapeutically effective amount of the inhibitor to be administered may need to be optimized for each individual. The pharmaceutical compositions may contain active ingredient in the range of about 0.1 to 2000 mg, preferably in the range of about 0.5 to 500 mg and most preferably between about 1 and 200 mg. A daily dose of about 0.01 to 100 mg/kg body weight, preferably between about 0.1 and about 50 mg/kg body weight, may be appropriate. The daily dose can be administered in one to four doses per day.

Abbreviations: "PPARγ" is used to refer to peroxisome proliferator-activated receptor γ; "AR" is used to refer to androgen receptor; "shRNA" is used to refer to short hairpin RNA; "PSA" is used to refer to prostate specific antigen; "FBS" is used to refer to fetal bovine serum; "RT-PCR" is used to refer to reverse transcriptase-polymerase chain reaction; "PPRE" is used to refer to peroxisome proliferator-activated receptor (PPAR) response element; "TBST" is used to refer to tris-buffered saline containing 0.1% Tween 20; and "compound(s)" refers to both (R) and (S) enantiomers of the described compound(s).

During the course of investigation of the effect of the thiazolidinedione family of peroxisome proliferator-activated receptor (PPARγ) agonists on repressing prostate specific antigen (PSA), it was demonstrated that troglitazone and ciglitazone at high doses mediated PPARγ-independent transcriptional repression of androgen receptor (AR) in a tumor cell-specific manner. This PPARγ-independent suppression of AR expression might, in part, underlie the antiproliferative activity of troglitazone in prostate cancer cells, and is of translational value to the development of troglitazone and ciglitazone into potent AR-ablative agents.

Based on the finding that PPARγ agonist ciglitazone at high doses was able to mediate PPARγ-independent transcriptional repression of AR in a tumor cell-specific manner, Δ2CG, a PPARγ-inactive analogue of ciglitazone, was used to conduct lead optimization to develop a novel class of AR-ablative agents. Structure-activity analysis indicates a high degree of flexibility in realigning Δ2CG's structural moieties without compromising potency in AR repression, as evidenced by the higher AR-ablative activity of the permuted isomer 9 [5-(4-hydroxy-benzylidene)-3-(1-methyl-cyclohexylmethyl)-thiazolidine-2,4-dione]. Further modification of 9 gave rise to 12 [5-(4-hydroxy-3-trifluoromethyl-benzylidene)-3-(1-methyl-cyclohexylmethyl)-thiazolidine-2,4-dione] which completely inhibited AR expression in LNCaP cells at low μM concentrations. This AR downregulation led to growth inhibition in LNCaP cells through apoptosis induction. Moreover, the role of AR repression in the antiproliferative effect of compound 12 was validated by the differential inhibition of cell viability between androgen-responsive and androgen-nonresponsive cells.

The invention relates to the pharmacological exploitation of the PPARγ agonist ciglitazone to develop a novel class of AR-ablative agents. The lead optimization of ciglitazone to develop compound 12 consisted of three stages (FIG. 1B). Stage 1 was to abrogate ciglitazone's PPARγ agonist activity by introducing a double bond adjoining the terminal thiazolidinedione ring, leading to the PPARγ inactive analogue Δ2CG. Stage 2 was to structurally modify Δ2CG via three distinct strategies: (a) regioisomerization of the (1-methykyclohexyl)-methyl moiety to yield compound 1, (b) phenyl ring substitutions to give compounds 2-8, and (c) permutational rearrangement of the terminal cyclohexyl moiety to generate compound 9. In Stage 3, compound 9 underwent modifications at the terminal phenyl ring, generating two series of compounds, i.e., 10 and 11, and 12-19. These Δ2CG derivatives were synthesized according to general procedures described in FIG. 1C, and their ability to suppress AR expression in LNCaP cells was assessed by the AR promoter-luciferase reporter gene assay followed by Western blot analysis.

Results

Dissociation of the PPARγ activity does not affect the ability of Δ2CG to inhibit AR expression at both mRNA and protein levels in LNCaP cells. Dose- and/or time-dependent effects of ciglitazone and Δ2CG on suppressing AR expression were assessed in LNCaP cells in 10% fetal bovine serum (FBS) by Western blotting and reverse transcriptase-polymerase chain reaction (RT-PCR). These analyses indicate that Δ2CG, albeit lacking PPARγ agonist activity, exhibited modestly higher potency than ciglitazone in mediating transcriptional repression of AR. For example, the concentrations required for complete suppression of AR protein expression were approximately 30 μM and 60 μM for Δ2CG and ciglitazone, respectively (FIG. 2A).

Figure 2:
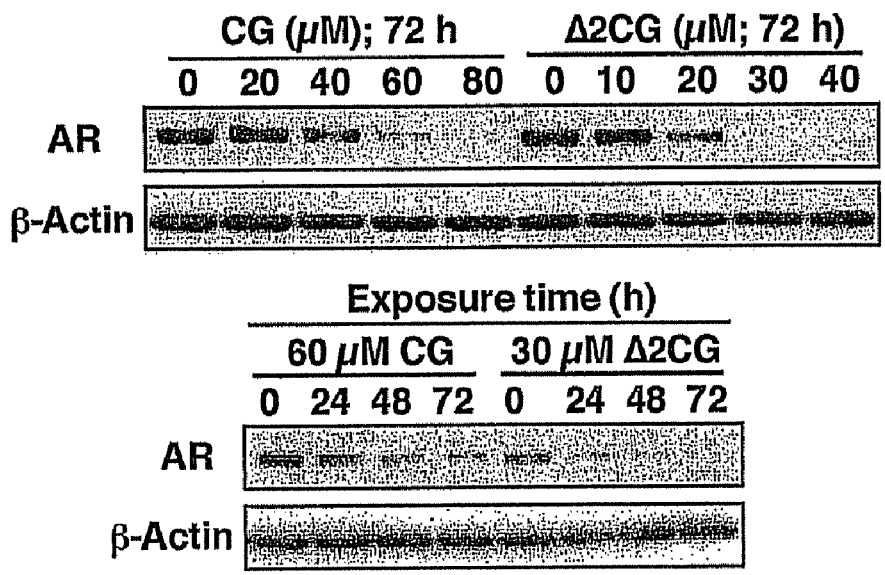
FIG. 2. Shows the effect of ciglitazone (CG) and Δ2CG on AR ablation in LNCaP cells. (A) Shows dose- and time-dependent effects of CG and Δ2CG on suppressing AR protein expression levels. Cells were exposed to CG or Δ2CG under the indicated conditions in 10% FBS-supplemented medium, and the lysates were subjected to Western blot analysis. (B) Shows time-dependent effect of CG (60 μM) and Δ2CG (30 μM) on suppressing the mRNA levels of AR. Cells were treated with either agent in 10% FBS-supplemented medium for the indicated times. Total RNA was isolated and subjected to RT-PCR analysis.
Figure 2:
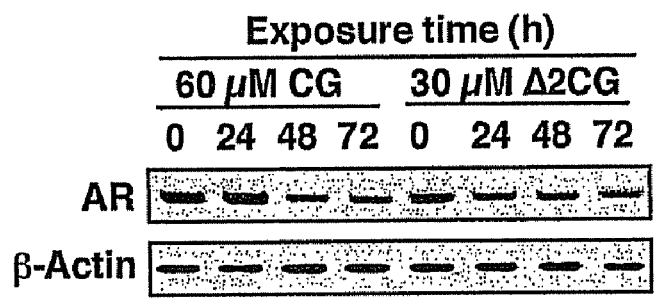

Furthermore, RT-PCR analysis indicates that the downregulation of AR expression occurred at the transcriptional level (FIG. 2B). Together, these findings confirmed the ability of ciglitazone to ablate AR independently of PPARγ activation, which provided a molecular rationale to use Δ2CG as a starting point for lead optimization to generate potent AR-ablative agents. To expedite the screening of AR-ablative agents, we used a luciferase reporter assay to analyze the effect of individual derivatives on suppressing AR transcription by using LNCaP cells transiently transfected with the AR promoter-linked luciferase reporter plasmid.

Figure 3:
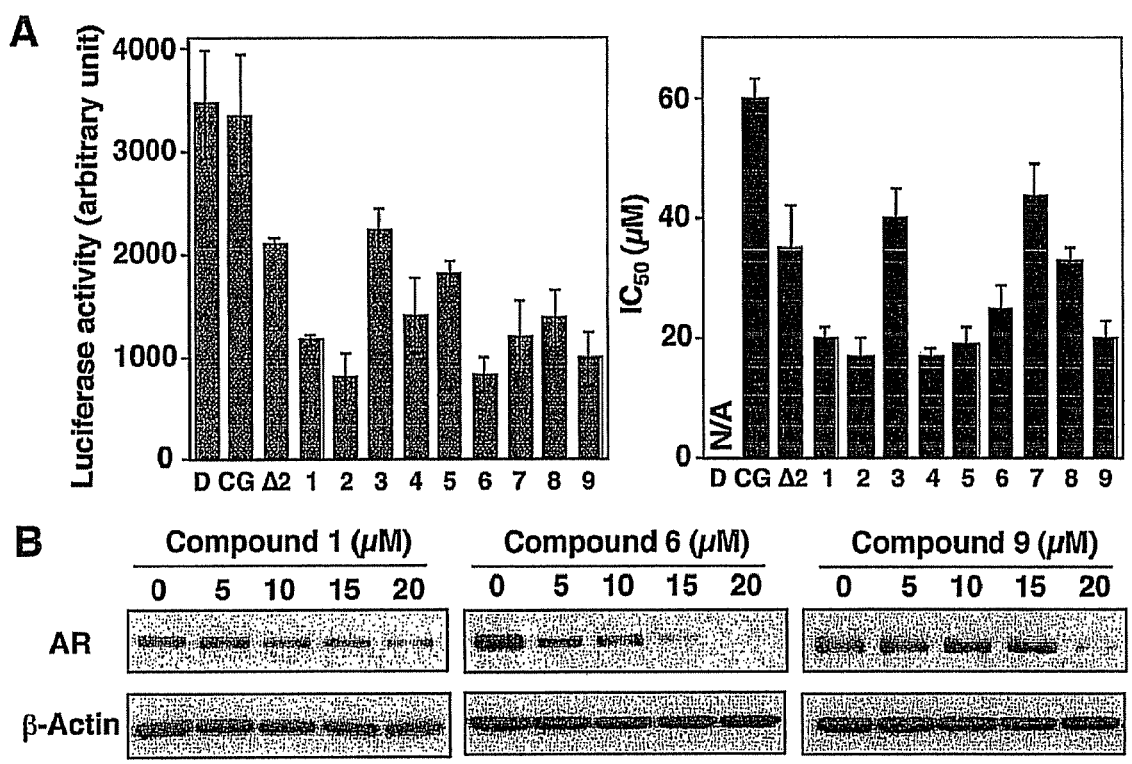
FIG. 3. Shows differential effects of ciglitazone, Δ2CG, and compounds 1-9 on suppressing AR expression in LNCaP cells. (A) The left panel shows analysis of the effects of individual compounds on the transcriptional repression of the AR gene by the AR promoter-luciferase reporter assay. LNCaP cells were transiently transfected with an AR promoter-linked luciferase reporter plasmid and exposed to DMSO vehicle (D), ciglitazone (CG, 20 μM), Δ2CG (Δ2, 20 μM), or compounds 1-9 (10 μM) in 10% FBS-supplemented RPMI 1640 medium for 48 h. Columns, mean (n=3); bars, standard deviation (SD). The right panel shows the $IC_{50}$ values of individual agents in inhibiting the cell viability of LNCaP cells. Cells were exposed to individual agents at various concentrations in 5% FBS-supplemented RPMI 1640 medium for 48 h, and cell viability was assessed by MTT assays. (B) Shows western blot analysis of the dose-dependent effect of compounds 1, 6, and 9 on reducing AR protein levels. Cells were exposed to individual agents at the indicated concentrations in 10% FBS-supplemented medium for 72 h, and the lysates were subjected to Western blot analysis.

Lead optimization of Δ2CG. As aforementioned, Δ2CG underwent three types of structural modifications, leading to compounds 1-9. Individual derivatives at 10 μM, compared to ciglitazone and Δ2CG, each at 20 μM, were evaluated in the luciferase reporter assay in the transiently transfected LNCaP cells. Relative to Δ2CG, these derivatives showed improved potency in suppressing the activity of the AR promoter, suggesting that a high degree of flexibility existed in the structure-activity relationship. This premise was borne out by the regioisomer 1 and the permuted isomer 9, both of which showed enhanced AR-ablating activity despite substantial configuration changes (FIG. 3A, left panel). Moreover, examination of the $IC_{50}$ values of individual derivatives in suppressing the viability of LNCaP cells after 48 hours of treatment indicates a positive correlation between the ability to suppress AR mRNA transcription and that of inhibiting cell viability (FIG. 3A).

Of these derivatives, compounds 1, 6, and 9 were chosen as representatives to conduct Western blot analysis. As shown in FIG. 3B, these three derivatives showed a dose-dependent effect on suppressing AR protein expression (FIG. 3B). In light of the unique structural feature of compound 9, this permuted derivative was used to carry out further structural optimization, generating compounds 10-19. The luciferase reporter analysis and cell viability assay indicated a subtle structure-activity relationship among these derivatives (FIG. 4A).

For example, moving the terminal para-OH function to the ortho or meta position (compounds 10 and 11) abolished the ability to suppress AR promoter-luciferase activity and cell viability, indicating its important role in interacting with the target protein. Moreover, substitutions of the phenyl ring with $CF_3$ or Br led to substantially higher potency in AR repression, while those with $NO_2$ or electron-donating groups attenuated the activity (FIG. 4A). Of these derivatives, compounds 12 and 16 represented the optimal agents in inhibiting AR mRNA transcription and LNCaP cell viability.

To demonstrate that this drug-induced transcriptional repression of AR was independent of PPARγ, the ability of compounds 12 and 16 versus troglitazone, ciglitazone, and Δ2CG to transactivate PPARγ by using the PPAR response element (PPRE)-luciferase reporter assay was examined. In PC-3 cells transfected with a reporter construct (PPRE-x3-TK-Luc), troglitazone and ciglitazone at 10 μM exhibited a significant effect on increasing luciferase activity, ranging from 2.5-fold to 4-fold (P<0.05). In contrast, compounds 12 and 16, like their parent compounds Δ2CG, lacked appreciable activity in PPARγ activation.

Figure 4:
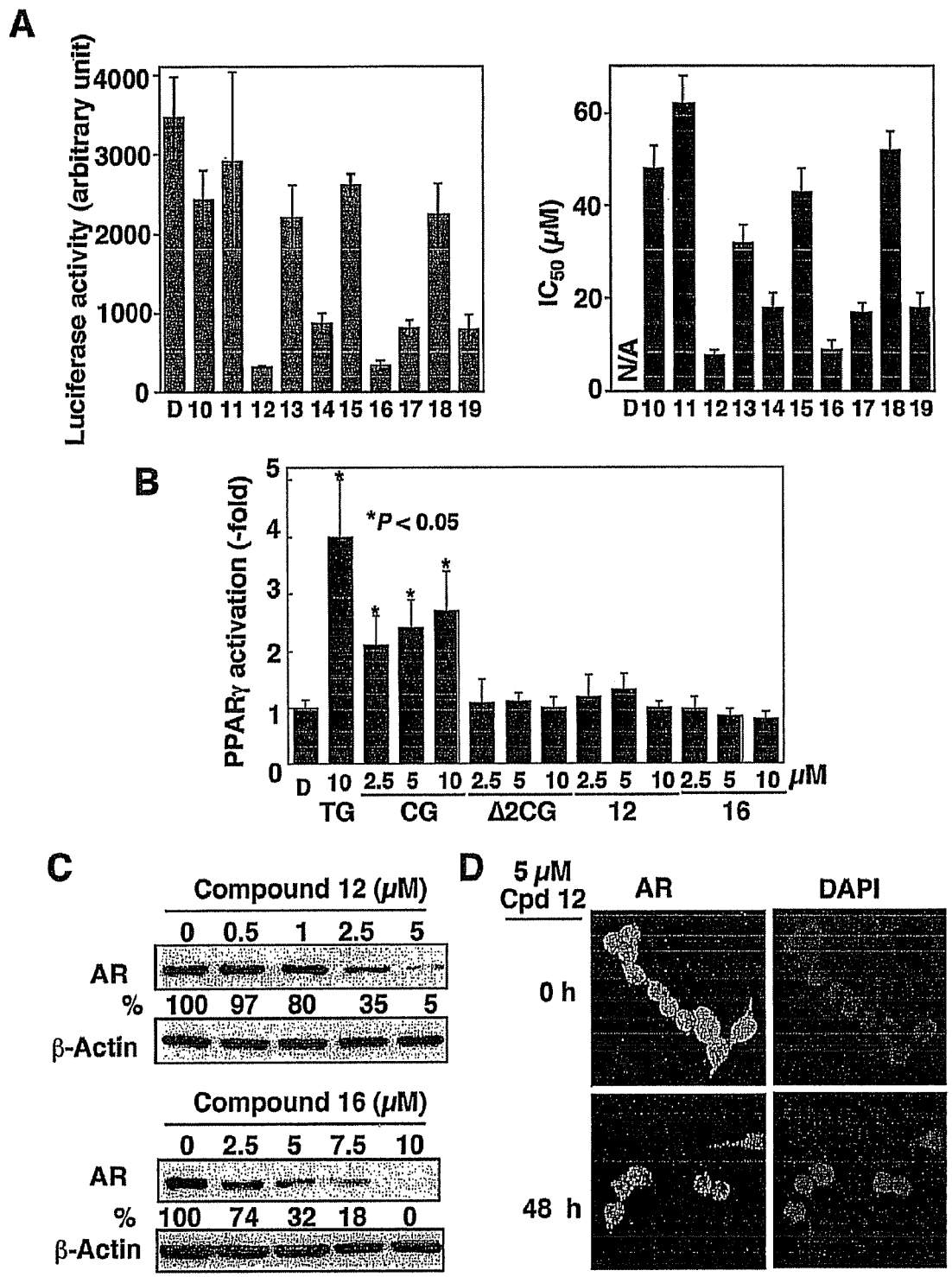
FIG. 4. Shows differential effect of compounds 10-19 on suppressing AR expression in LNCaP cells. (A) The left panel shows analysis of the effects of DMSO vehicle (D) or individual compounds on the transcriptional repression of the AR gene by the AR promoter-luciferase-reporter assay. LNCaP cells were transiently transfected with an AR promoter-linked luciferase reporter plasmid and exposed to compounds 10-19 (10 μM) in 10% FBS-supplemented RPMI 1640 medium for 48 h. Analysis of luciferase activity was carried out as described in the Experimental Section. Columns, mean (n=3); bars, SD. The right panel shows the $IC_{50}$ values of individual agents in inhibiting the cell viability of LNCaP cells. Cells were exposed to individual agents at various concentrations in 5% FBS-supplemented RPMI 1640 medium for 48 h, and cell viability was assessed by MTT assays. (B) Shows the dose-dependent effect of ciglitazone (CG), Δ2CG, and compounds 12 and 16, relative to that of 10 μM troglitazone (TG), on PPARγ activation in PC-3 cells. PC-3 cells were transiently transfected with PPRE-x3-TK-Luc reporter vector and then exposed to individual agents or DMSO vehicle (D) in 10% FBS-supplemented RPMI 1640 medium for 48 h. Columns, mean (n=6); bars, SD. (C) Shows western blot analysis of the dose-dependent effect of compounds 12 and 16, on reducing AR protein levels. Cells were exposed to individual agents at the indicated concentrations in 10% FBS-supplemented medium for 72 h, and the lysates were subjected to Western blot analysis. (D) Shows immunocytochemical analysis of the effect of 5 µM compound 12 on suppressing AR expression after 24-h exposure. The nuclear counterstaining was achieved using a 4',6-diamino-2-phenylindole (DAPI)-containing mounting medium.

Western blot analysis indicates that the $IC_{50}$ values for suppressing AR expression by compounds 12 and 16 after 72-h exposure were approximately 2 μM and 4 μM, respectively (FIG. 4C). The ability of compound 12 to suppress AR expression was further demonstrated by immunocytochemical analysis (FIG. 4D). As shown, exposure of LNCaP cells to 5 μM compound 12 for 48 h led to a substantial decrease in AR levels in the nucleus.

Antitumor effects of compound 12 in prostate cancer cells. The antitumor effects of compound 12 were assessed in both LNCaP androgen-responsive and PC-3 androgen-nonresponsive prostate cancer cells via three different methods, including the MTT assay for cell viability, cell counting for cell proliferation, and flow cytometric analysis for cell cycle distribution. Due to lack of AR expression, PC-3 cells exhibited substantially lower sensitivity to the antiproliferative activities of compound 12 as compared to LNCaP cells. The $IC_{50}$ values for suppressing cell viability were 8 μM and 3 μM, at 48 h and 72 h of drug treatment, respectively, in LNCaP cells, and 15 μM and 12 μM, respectively, in PC-3 cells (FIG. 5A).

Figure 5:
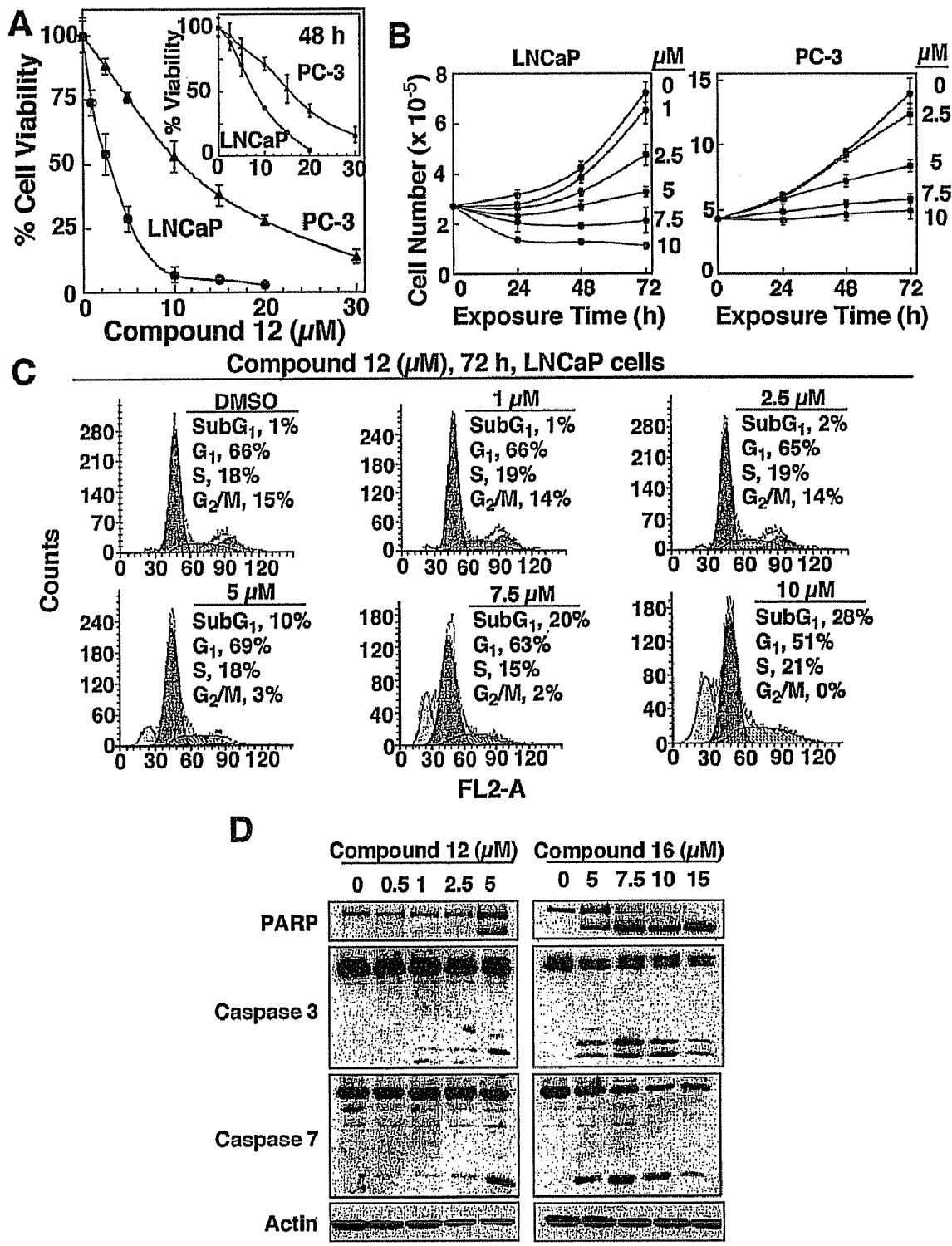
FIG. 5. Shows antitumor effects of compound 12 in LNCaP cells. (A) Shows differential dose-dependent effects of compound 12 on the inhibition of cell viability of LNCaP versus PC-3 cells at 48 h (inset) and 72 h of treatment. Cells were exposed to the indicated concentrations of compound 12 in 5% FBS-containing RPMI 1640 medium for 48 and 72 h, and cell viability was determined by MTT assays. Points, mean (n=6); bars, SD. (B) Shows dose- and time-dependent antiproliferative effects of compound 12 in LNCaP (left panel) and PC-3 (right panel) cells. Cells were seeded into six-well plates (250,000 cells/well), incubated for 24 h, and exposed to compound 12 at the indicated concentrations in 5% FBS-supplemented medium for different time intervals. Cells were harvested, and counted using a Coulter counter. (C) Shows flow cytometric analysis of LNCaP cells after treatment with DMSO or the indicated concentrations of compound 12 for 72 h. Percentages of cell cycle distribution represent the mean of two independent determinations. (D) Shows western blot analysis of the dose-dependent effects of compounds 12 and 16 on PARP cleavage, caspase 3 activation, and caspase 7 activation in LNCaP cells after 72 h of treatment.

This differential susceptibility was also manifest in the cell counting assay, in which compound 12 exhibited at least twofold higher potency in inhibiting the proliferation of LNCaP cells as compared to PC-3 cells (FIG. 5B). Moreover, cell cycle analysis was carried out after exposing LNCaP cells to different doses of compound 12 for 72 h (FIG. 5C). As shown, compound 12 caused a dose-dependent increase in the sub-$G_1$ population, accompanied by decreases in the $G_2$/M phase (FIG. 5C). Furthermore, the ability of compounds 12 and 16 to induce apoptotic death in LNCaP cells was demonstrated by their dose-dependent effects on modulating various apoptosis-related biomarkers, including PARP cleavage, and the proteolytic activation of caspase 3 and caspase 7 (FIG. 5D).

Figure 6:
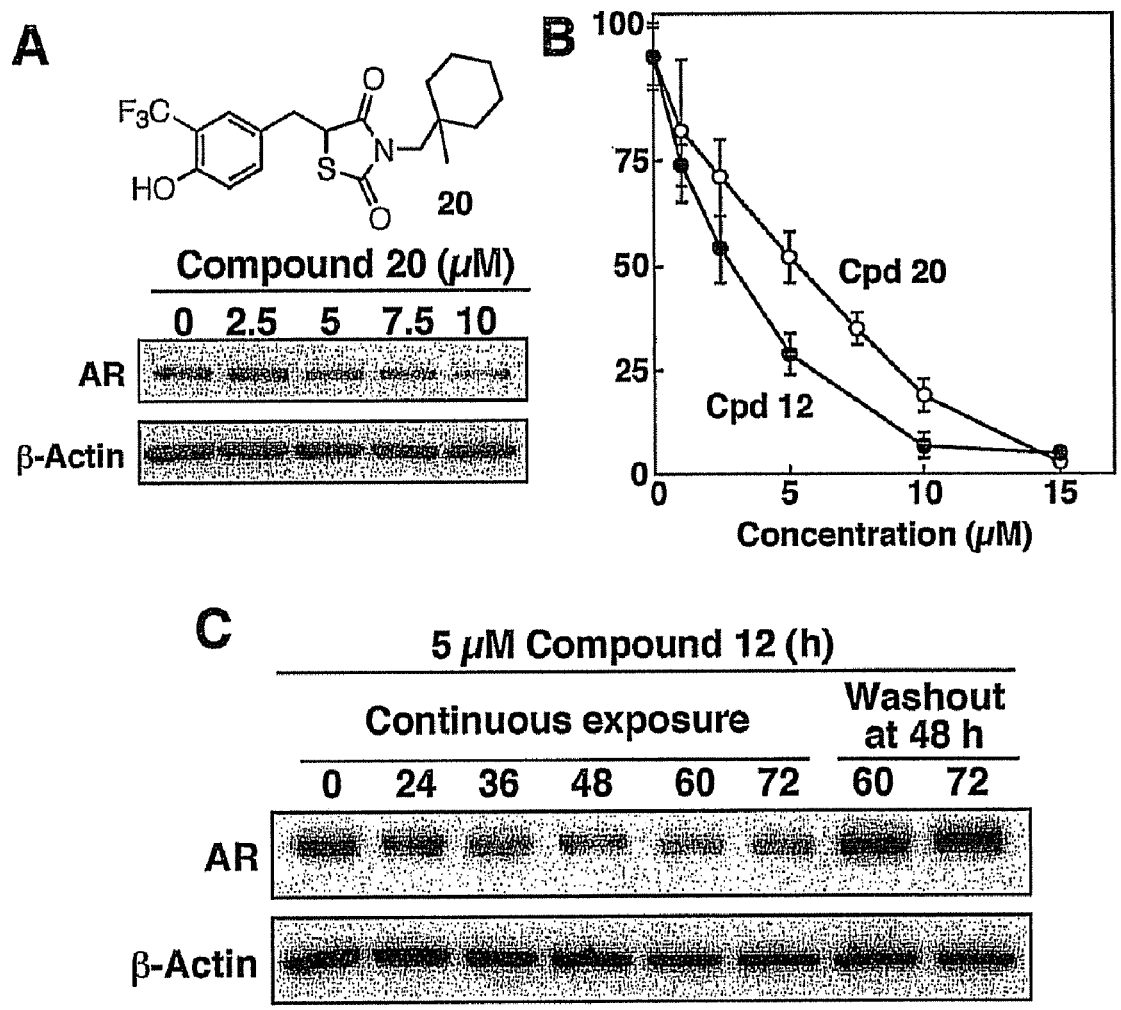
FIG. 6. Shows evidence that the ability of compound 12 to inhibit AR expression in LNCaP cells is not mediated through an irreversible mechanism. (A) Shows the structure and dose-dependent effect of compound 20 on suppressing AR expression in LNCaP cells. Cells were exposed to compound 20 at the indicated concentrations in 10% FBS-supplemented medium for 72 h, and the lysates were subjected to Western blot analysis. (B) Shows the dose-dependent effects of compound 12 versus compound 20 in suppressing the viability of LNCaP cells. Cells were exposed to individual agents at various concentrations in 5% FBS-supplemented RPMI 1640 medium for 48 h, and cell viability was assessed by MTT assays. (C) Shows restoration of AR expression in LNCaP cells after compound 12 was washed out. The effect of 5 µM compound 12 on AR repression in LNCaP cells was examined at different intervals throughout a 72 h-period in two different manners. Continuous exposure: cells in T-25 flasks were incubated in drug-containing, 10% FBS-supplemented medium for 72 h, and washout at 48 h of treatment: cells in T-25 flasks were exposed to the agent for 44 h, followed by incubation in drug-free medium for additional 24 h. AR levels in cell lysates were analyzed by Western blot analysis.

An earlier study indicated that thiazolidinediones mediated the transcriptional repression of AR by facilitating the degradation of the transcription factor Sp1. However, it was reported that compounds containing a 5-arylidene-3-aryl-2,4-thiazolidinedione substructure underwent conjugation addition with p-thiocresol in the presence of piperidine upon heating. This raised the possibility that compound 12 and other derivatives might act as "Michael acceptors" by covalently modify the target enzyme/protein upon binding. Two lines of evidence were obtained to refute this possibility. First, compound 20, a saturated counterpart of compound 12, retained the ability to suppress AR expression and cell viability, though with slightly lower potency, in LNCaP cells (FIGS. 6A and B). Second, the expression level of AR in drug-treated LNCaP cells would be rapidly restored once compound 12 was removed (or washed out) from the medium (FIG. 6C). This rapid restoration of the AR expression suggests a reversible nature of this ligand-protein interaction.

Discussion

In light of the pivotal role of PPARγ in prostate cell proliferation and differentiation, the chemopreventive activity of thiazolidinediones in prostate cancer has been attributed to their ability to activate PPARγ signaling, leading to the terminal differentiation and growth arrest of tumor cells. However, mounting evidence suggests that the antiproliferative ability of these agents is independent of their PPARγ agonist activity. The inventors have identified several "off-target" mechanisms that might underlie the antitumor effects of thiazolidinediones, including Bcl-2/Bcl-xL inhibition, proteasomal degradation of cyclin D1, β-catenin, and Sp1, and transcriptional repression of PSA and AR. Separation of these pharmacological effects from PPARγ activation provides a mechanistic rationale for using thiazolidinediones as a scaffold to develop potent molecularly targeted agents. Considering the importance of AR in prostate tumorigenesis and tumor progression, lead optimization of ciglitazone and its PPARγ-inactive derivative Δ2CG was carried out to develop potent AR-ablative agents.

There existed a high degree of tolerance for the substructural rearrangement of Δ2CG without compromising the AR-ablative activity, as evidenced by the improved potency of compounds 1 and 9. In contrast, modifications of the phenyl ring exhibited a subtle effect on the AR-ablative potency. For example, changing the orientation of the terminal hydroxyl function of compound 9 completely abrogated the ability of the resulting compounds 10 and 11 to suppress AR expression, while the $CF_3$- or di-Br-substitution led to enhanced potency. Together, these findings suggest that the benzylidene-thiazolidinedione substructure played a crucial role in interacting with the target protein.

Among all derivatives examined, compound 12 represented a structurally optimized derivative with an-order-of-magnitude higher potency than ciglitazone in suppressing AR expression. This AR downregulation led to growth inhibition in LNCaP cells through apoptosis induction, as evidenced by flow cytometry, PARP cleavage and caspase activation. The role of AR repression in the antiproliferative effect of compound 12 was supported by the differential inhibition of cell viability between LNCaP androgen-responsive and PC-3 androgen-nonresponsive cells. Because thiazolidinediones mediate AR repression through downregulation of Sp1, compound 12 also suppresses the transcription of many Sp1-targeted genes (data not shown), which accounts for the ability of compound 12 to inhibit PC-3 cell viability.

Relative to many natural product-based agents that suppress AR expression/function, such as resveratrol, vitamin E succinate, genistein, and curcumin, compound 12 is substantially more effective in downregulating AR expression. Thus, this AR-ablative agent has translational potential to foster new therapeutic strategies for prostate cancer treatment as a single agent or in combination with other molecularly targeted agents.

Conclusion

The in vivo efficacy of targeting AR expression to block tumor growth and delaying tumor progression has recently been demonstrated in a LNCaP tumor xenograft model by using shRNA-mediated AR knockdown. This finding provides a proof-of-principle that inhibition of AR expression represents a therapeutically relevant strategy for prostate cancer treatment.

Compound Preparation

Compounds of the invention may be synthesized by synthetic routes that include processes derivativeous to those well known in the chemical arts, particularly in light of the description contained herein. The starting materials are generally available from commercial sources such as Aldrich Chemicals (Milwaukee, Wis., USA) or are readily prepared using methods well known to those skilled in the art (e.g., prepared by methods generally described in Louis F. Fieser and Mary Fieser, Reagents for Organic Synthesis, v. 1-19, Wiley, New York, (1967-1999 ed.); Alan R. Katritsky, Otto Meth-Cohn, Charles W. Rees, Comprehensive Organic Functional Group Transformations, v 1-6, Pergamon Press, Oxford, England, (1995); Barry M. Trost and Ian Fleming, Comprehensive Organic Synthesis, v. 1-8, Pergamon Press, Oxford, England, (1991); or Beilsteins Handbuch der organischen Chemie, 4, Aufl. Ed. Springer-Verlag, Berlin, Germany, including supplements (also available via the Beilstein online database)).

For illustrative purposes, the reaction schemes depicted in the EXAMPLES below provide potential routes for synthesizing the compounds of the present invention as well as key intermediates. The EXAMPLES provide detailed description of the individual reaction steps and also provide general synthetic routes that can be used to prepare a families of related compounds.

Those skilled in the art will appreciate that other synthetic routes may be used to synthesize the compounds of the invention. Although specific starting materials and reagents are depicted in the reaction schemes and discussed below, other starting materials and reagents can be easily substituted to provide a variety of derivatives and/or reaction conditions. In addition, many of the compounds prepared by the methods described below can be further modified in light of this disclosure using conventional methods well known to those skilled in the art.

EXAMPLES

Further details of the invention can be found in the following examples, which further define the scope of the invention.

Example 1

Synthesis of Androgen Receptor-Ablative Agents

Chemical reagents and organic solvents were purchased from Sigma-Aldrich unless otherwise mentioned. Nuclear magnetic resonance spectra ($^1$H NMR) were measured on a Bruker DPX 300 model spectrometer. Chemical shifts ($\delta$) were reported in parts per million (ppm) relative to the TMS peak. Electrospray ionization mass spectrometry analyses were performed with a Micromass Q-T of II High-Resolution electrospray mass spectrometer. Elemental analyses were performed by the Atlantic Microlab, Inc. (Norcross, Ga.), and were reported within 0.4% of calculated values. Flash column chromatography was performed with silica gel (230-400 mesh). Δ2CG and the two series of compounds, 1-8 and 9-19, were synthesized according to the general methods described in FIG. 1B, which are illustrated by the synthesis of compounds 1 and 9 as examples.

5-[3-(1-Methyl-cyclohexylmethoxy)-benzylidene]-thiazolidine-2,4-dione (1)

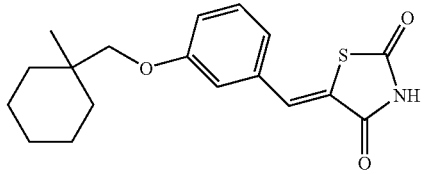

Step a: To a stirring solution of LiAlH$_4$ (20 mmol) in anhydrous THF (10 mL) at 4° C. was added 1-methyl-cyclohexanecarboxylic acid (i, 7.0 mmol) in 50 mL of THF dropwise over a period of 1 hour. The solution was stirred at refluxing temperature under N$_2$ for 6 hours. The solution was cooled to 4° C. by ice bath, and 1 mL of 1 N NaOH (1 mL) followed by H$_2$O (2 mL) was slowly added to the solution to quench the reaction. The solution was stirred at 23° C. for 1 hour and then filtered to remove solid material. The solution was concentrated. Purification by flash silica gel chromatography (ethyl acetate/hexanes, 1:2) gave the product, (1-methyl-cyclohexyl)-methanol (ii), in 82% yield.

Step b. A solution of compound ii (1 mmol) in dry CH$_2$Cl$_2$ (5 mL) was cooled to 4° C., to which was added pyridine (1.1 mmol) and triflate anhydride (1.1 mmol). After stirring at 4° C. for 2 h, the solution was concentrated, and the residue was purified by flash silica gel column chromatography (ethyl acetate/hexanes, 1:10) to afford trifluoro-methanesulfonic acid 1-methyl-cyclohexylmethyl ester (iii) in 35% yield.

Step c. A mixture of compound iii (0.5 mmol), 3-hydroxybenzaldehyde (iv, 0.6 mmol) and K$_2$CO$_3$ (0.7 mmol) were dissolved in DMF (3 mL). The solution was heated to 80° C. for 4 hr. The solution was poured into water, extracted with ethyl acetate (10 mL) three times, and concentrated. The residue was purified by chromatography and resulted in 0.22 mmol of 3-(1-methyl-cyclohexylmethoxy)-benzaldehyde (v) with a 44% yield.

Step d. A mixture consisting of compound v (0.5 mmol), 2,4-thiazolidinedione (0.6 mmol) and catalytic amounts of piperidine was refluxed in EtOH (5 mL) for 24 h and then concentrated. The oily product was dissolved in ethyl acetate, poured into water and acidified with AcOH. The solution was extracted with ethyl acetate, dried and concentrated. The residue was purified by silica gel chromatography, providing compound 1 in 67% yield. ¹H NMR (300 MHz, CDCl₃) δ 1.04 (s, 3H), 1.46-1.56 (m, 10H), 3.69 (s, 2H), 6.78-7.28 (m, 2H), 7.08 (d, J=8.40 Hz, 1H), 7.39 (dt, J=2.10, 8.40 Hz, 1H), 7.84 (s, 1H), 8.21-8.78 (br, 1H); HRMS exact mass of (M+Na)⁺, 354.1140 amu; observed mass of (M+Na)⁺, 354.113 amu.

5-[3-Bromo-4-(1-methyl-cyclohexylmethoxy)-benzylidene]-thiazolidine-2,4-dione (2)

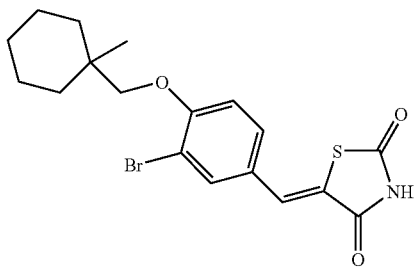

¹H NMR (300 MHz, CDCl₃) δ 1.11 (s, 3H), 1.40-1.61 (m, 10H), 3.77 (s, 2H), 6.95 (d, J=8.42 Hz, 1H), 7.41 (dd, J=2.10, 8.42 Hz, 1H), 7.69 (d, 1H, J=2.10), 7.74 (s, 1H), 8.38 (s, 1H); HRMS exact mass of (M+Na)⁺, 432.0245 amu, observed mass of (M+Na)⁺, 432.0247 amu.

5-[4-(1-Methyl-cyclohexylmethoxy)-3-nitro-benzylidene]-thiazolidine-2,4-dione (3)

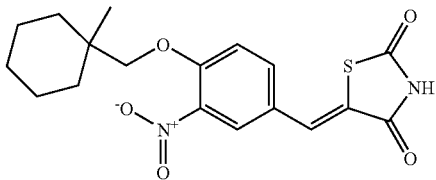

¹H NMR (300 MHz, CDCl₃) δ 1.08 (s, 3H), 1.42-1.59 (m, 10H), 3.79 (s, 2H), 7.23 (d, J=8.40 Hz, 1H), 7.85 (d, J=8.42 Hz, 1H), 7.92 (s, 1H), 8.10 (s, 1H), 8.33 (s, 1H); HRMS exact mass of (M+Na)⁺, 399.0991 amu; observed mass of (M+Na)⁺, 399.0995 amu.

5-[4-(1-Methyl-cyclohexylmethoxy)-3-trifluoromethyl-benzylidene]-thiazolidine-2,4-dione (4)

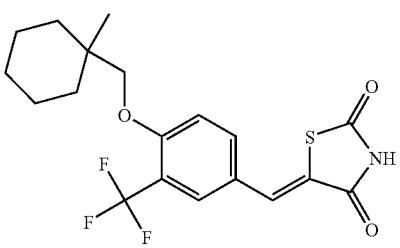

¹H NMR (300 MHz, CDCl₃) δ 1.08 (s, 3H), 1.42-1.59 (m, 10H), 3.79 (s, 2H), 7.10 (d, J=8.40 Hz, 1H), 7.63 (d, J=8.42 Hz, 1H), 7.71 (s, 1H), 7.80 (s, 1H), 8.09-8.12 (br, 1H), HRMS exact mass of (M+Na)⁺, 422.1014 amu; observed mass of (M+Na)⁺, 422.1019 amu.

5-[3-Methoxy-4-(1-methyl-cyclohexylmethoxy)-benzylidene]-thiazolidine-2,4-dione (5)

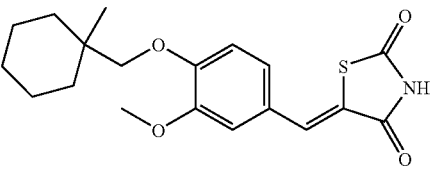

¹H NMR (300 MHz, CDCl₃) δ 1.09 (s, 3H), 1.40-1.58 (m, 10H), 3.75 (s, 2H), 3.96 (s, 3H), 6.96 (d, J=8.40 Hz, 1H), 7.00 (s, 1H), 7.11 (d, J=8.42 Hz, 1H), 7.79 (s, 1H), 8.55 (s, 1H); HRMS exact mass of (M+Na)⁺, 384.1245 amu; observed mass of (M+Na)⁺, 384.1239 amu.

5-[3-Ethoxy-4-(1-methyl-cyclohexylmethoxy)-benzylidene]-thiazolidine-2,4-dione (6)

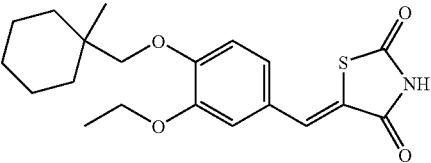

¹H NMR (300 MHz, CDCl₃) δ 1.08 (s, 3H), 1.40-1.58 (m, 13H), 3.74 (s, 2H), 4.10 (q, J=6.9 Hz, 2H), 6.95 (d, J=8.40 Hz, 1H), 7.01 (d, J=2.10 Hz, 1H), 7.11 (dd, J=8.40, 2.10 Hz, 1H), 7.79 (s, 1H), 8.42 (s, 1H); HRMS exact mass of (M+Na)⁺, 389.1402 amu; observed mass of (M+Na)⁺, 389.1402 amu,

5-[3,5-Dimethyl-4-(1-methyl-cyclohexylmethoxy)-benzylidene]-thiazolidine-2,4-dione (7)

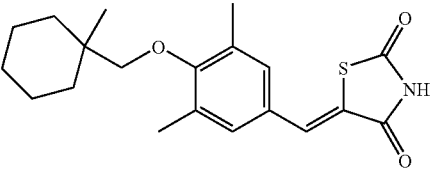

¹H NMR (300 MHz, CDCl₃) δ 1.13 (s, 3H), 1.32-1.59 (m, 10H), 2.42 (s, 6H), 3.48 (s, 2H), 7.17 (s, 2H), 7.76 (s, 1H), 8.26 (s, 1H); HRMS exact mass of (M+Na)⁺, 382.1453 amu; observed mass of (M+Na)⁺, 382.1448 amu.

5-[4-(1-Methyl-cyclohexylmethoxy)-naphthalen-1-ylmethylene]-thiazolidine-2,4-dione (8)

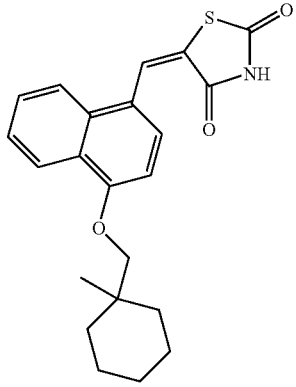

¹H NMR (300 MHz, CDCl₃) δ 1.18 (s, 3H), 1.51-1.59 (m, 10H), 3.91 (s, 2H), 6.915 (d, J=8.70 Hz, 1H), 7.55-7.69 (m, 3H), 8.12 (d, J=8.70 Hz, 1H), 8.39 (d, J=8.40 Hz, 1H), 8.59 (s, 1H); HRMS exact mass of (M+Na)⁺, 404.1296 amu; observed mass of (M+Na)⁺, 404.1299 amu.

5-(4-Hydroxy-benzylidene)-3-(1-methyl-cyclohexyl-methyl)-thiazolidine-2,4-dione (9)

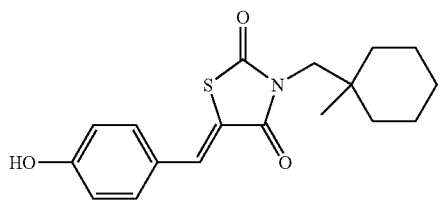

Step e. A mixture of p-hydroxybenzaldehyde (vi; 0.5 mmol), 2,4-thiazolidinedione, (0.6 mmol), and catalytic amounts of piperidine and AcOH was refluxed in toluene (5 mL) for 24 h. The precipitated product was filtered, washed with toluene (3×10 mL), and dried in vacuo at 60° C. overnight, yielding 5-(4-hydroxybenzylidene)-thiazolidine-2,4-dione (vii) in a 85% yield.

Step f. A solution of compound vii (0.5 mmol), compound iii (0.6 mmol) and K₂CO₃ (0.65 mmol) were stirred in DMF (3 mL) at 80° C. for 4 hr, poured into water, extracted with ethyl acetate (3×10 mL), dried and concentrated. The residue was purified by chromatography, affording compound 9 in 42% yield. ¹H NMR (300 MHz, CDCl₃) δ 0.94 (s, 3H), 1.14-1.86 (m, 10H), 3.63 (s, 2H), 5.69 (s, 1H), 6.94 (d, J=8.40 Hz, 2H), 7.43 (d, J=8.40 Hz, 2H), 7.83 (s, 1H); HRMS exact mass of (M+Na)⁺, 354.1140 amu; observed mass of (M+Na)⁺, 354.1141 amu.

5-(2-Hydroxy-benzylidene)-3-(1-methyl-cyclohexyl-methyl)-thiazolidine-2,4-dione (10)

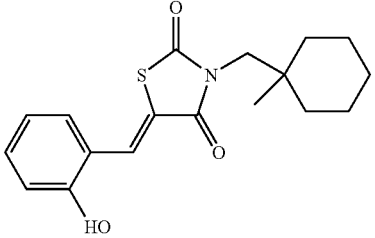

1H NMR (300 MHz, CDCl₃) δ 0.95 (s, 3H), 1.22-1.65 (m, 10H), 3.66 (s, 2H), 6.44 (d, J=0.9 Hz, 1H), 6.91 (dd, J=8.10, 0.9 Hz, 1H), 7.04 (td, J=7.2, 0.6 Hz, 1H), 7.32 (tdd, J=7.5, 1.5, 0.6 Hz, 1H), 7.46 (dd, J=7.80, 1.5 Hz, 1H), 8.42 (s, 1H); HRMS exact mass of (M+Na)⁺, 354.1140 amu; observed mass of (M+Na)⁺, 354.1145 amu.

5-(3-Hydroxy-benzylidene)-3-(1-methyl-cyclohexyl-methyl)-thiazolidine-2,4-dione (11)

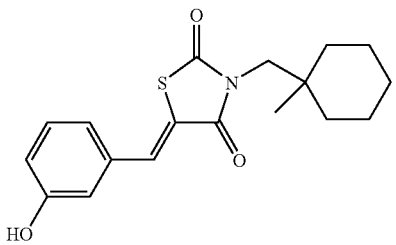

¹H NMR (300 MHz, CDCl₃) δ 0.96 (s, 3H), 1.24-1.67 (m, 10H), 3.65 (s, 2H), 5.24 (s, 1H), 6.70 (d, J=1.5 Hz, 1H), 6.93 (dd, J=8.10, 1.5 Hz, 1H), 7.10 (d, J=7.80 Hz, 1H), 7.36 (dd, J=7.80, 7.50 Hz, 1H), 7.84 (s, 1H); HRMS exact mass of (M+Na)⁺, 354.1140 amu; observed mass of (M+Na)⁺, 354.1143 amu.

5-(4-Hydroxy-3-trifluoromethyl-benzylidene)-3-(1-methyl-cyclohexylmethyl)-thiazolidine-2,4-dione (12)

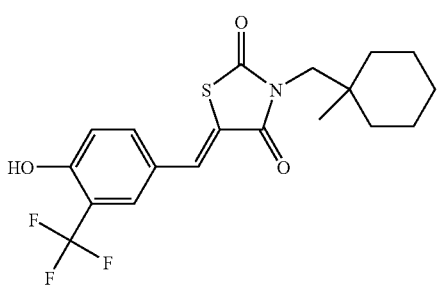

$^1$H NMR (300 MHz, CDCl$_3$) δ 0.95 (s, 3H), 1.46-1.56 (m, 10H), 3.64 (s, 2H), 6.08-6.38 (br, 1H), 7.09 (d, J=8.40 Hz, 1H), 7.59 (d, J=8.40 Hz, 1H), 7.69 (s, 1H), 7.83 (s, 1H); HRMS exact mass of (M+Na)$^+$, 422.1014 amu; observed mass of (M+Na)$^+$, 422.1012 amu. Anal. (C$_{19}$H$_{20}$F$_3$NO$_3$S) C, H, N, S, O, F.

5-(4-Hydroxy-3-nitro-benzylidene)-3-(1-methyl-cyclohexylmethyl)-thiazolidine-2,4-dione (13)

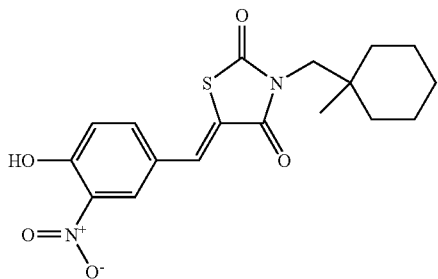

$^1$H NMR (300 MHz, CDCl$_3$) δ 0.96 (s, 3H), 1.23-1.57 (m, 10H), 3.68 (s, 2H), 7.31 (d, J=8.40 Hz, 1H), 7.74 (dd, J=8.40, 2.1 Hz, 1H), 7.81 (s, 1H), 8.29 (d, J=2.1 Hz, 1H); HRMS exact mass of (M+Na)$^+$, 399.0991 amu; observed mass of (M+Na)$^+$, 399.0991 amu.

5-(3-Bromo-4-hydroxy-benzylidene)-3-(1-methyl-cyclohexylmethyl)-thiazolidine-2,4-dione (14)

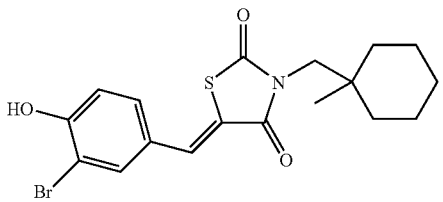

$^1$H NMR (300 MHz, CDCl$_3$) δ 0.79 (s, 3H), 1.17-1.46 (m, 10H), 3.36 (s, 2H), 7.01 (d, J=8.40 Hz, 1H), 7.37 (d, J=8.40 Hz, 1H), 7.73 (s, 2H); HRMS exact mass of (M+Na)$^+$, 432.0245 amu; observed mass of (M+Na)$^+$, 432.0245 amu. Anal. (C$_{18}$H$_{20}$BrNO$_3$S) C, H, N, O 5-(4-Hydroxy-3-methoxy-benzylidene)-3-(1-methyl-cyclohexylmethyl)-thiazolidine-2,4-dione (15)

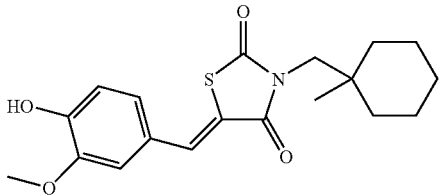

$^1$H NMR (300 MHz, CDCl$_3$) δ 0.92 (s, 3H), 1.21-1.58 (m, 10H), 3.62 (s, 2H), 3.97 (s, 3H), 5.95 (br, 1H), 6.90-7.03 (m, 2H), 7.10 (d, J=7.80 Hz, 1H), 7.82 (s, 1H), HRMS exact mass of (M+Na)$^+$, 384.1245 amu; observed mass of (M+Na)$^+$, 384.1245 amu. Anal. (C$_{19}$H$_{23}$NO$_4$S) C, H, N, O.

5-(3,5-Dibromo-4-hydroxy-benzylidene)-3-(1-methyl-cyclohexylmethyl)-thiazolidine-2,4-dione (16)

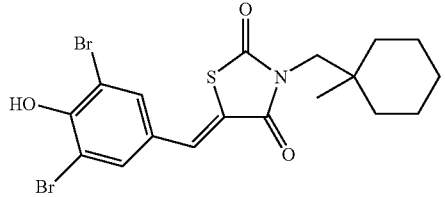

$^1$H NMR (300 MHz, CDCl$_3$) δ 0.94 (s, 3H), 1.32-1.56 (m, 10H), 3.63 (s, 2H), 6.22 (s, 1H), 7.62 (s, 2H), 7.68 (s, 1H); HRMS exact mass of (M+Na)$^+$, 511.9330 amu; observed mass of (M+Na)$^+$, 511.9329 amu. Anal. (C$_{18}$H$_{19}$Br$_2$NO$_3$S) C, H, N, S, O, Br.

5-(4-Hydroxy-3-iodo-5-methoxy-benzylidene)-3-(1-methyl-cyclohexylmethyl)-thiazolidine-2,4-dione (17)

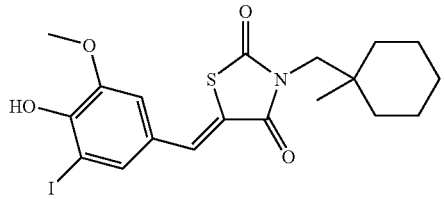

$^1$H NMR (300 MHz, CDCl$_3$) δ 0.94 (s, 3H), 1.22-1.62 (m, 10H), 3.63 (s, 2H), 3.96 (s, 3H), 6.44 (s, 1H), 6.97 (s, 1H), 7.50 (s, 1H), 7.73 (s, 1H), HRMS exact mass of (M+Na)$^+$, 510.0212 amu; observed mass of (M+Na)$^+$, 510.0213 amu.

5-(4-Hydroxy-3,5-dimethyl-benzylidene)-3-(1-methyl-cyclohexylmethyl)-thiazolidine-2,4-dione (18)

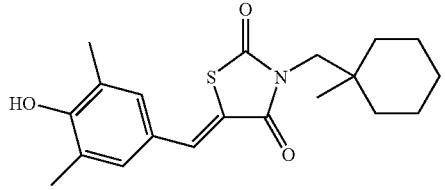

$^1$H NMR (300 MHz, CDCl$_3$) δ 0.94 (s, 3H), 1.22-1.66 (m, 10H), 2.30 (s, 6H), 3.62 (s, 2H), 5.06 (s, 1H), 7.17 (s, 2H), 7.78 (s, 1H); HRMS exact mass of (M+Na)$^+$, 382.1453 amu; observed mass of (M+Na)$^+$, 382.1454 amu.

5-(4-Hydroxy-naphthalen-1-ylmethylene)-3-(1-methyl-cyclohexylmethyl)-thiazolidine-2,4-dione (19)

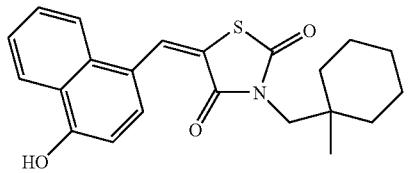

$^1$H NMR (300 MHz, CDCl$_3$) δ 0.98 (s, 3H), 1.20-1.66 (m, 10H), 3.67 (s, 2H), 5.91 (s, 1H), 6.91 (d, J=7.80 Hz, 1H), 7.56-7.67 (m, 3H), 8.15 (d, J=8.40 Hz, 1H), 8.29 (d, 1H, J=7.20 Hz), 8.60 (s, 1H); HRMS exact mass of (M+Na)$^+$, 404.1296 amu; observed mass of (M+Na)$^+$, 404.1296 amu.

5-(4-Hydroxy-3-trifluoromethyl-benzyl)-3-(1-methyl-cyclohexylmethyl)-thiazolidine-2,4-dione (20)

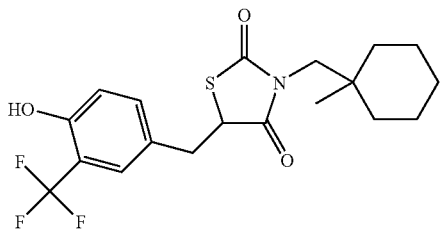

A mixture of compound 12 (20 mg) and Pd—C (40 mg) in methanol (5 mL) was stirred under hydrogen (50 psi) overnight, filtered, and concentrated to dryness under vacuum. The residue was purified by silica gel flash chromatography and re-crystallized with ethyl acetate-hexane (1:8), giving compound 20 (14 mg). $^1$H NMR (250 MHz, CDCl$_3$) 0.81 (s, 3H), 1.16-1.59 (m, 10H), 3.13 (dd, 1H, J=9.3 Hz, 8.7 Hz), 3.45 (s, 2H), 3.51 (dd, 1H, J=9.3 Hz, 3.6 Hz), 4.44 (dd, 1H, J=3.6 Hz, 8.7 Hz), 5.53 (s, 1H), 6.92 (d, 1H, J=8.40 Hz), 7.33 (d, 1H, J=8.40 Hz), 7.39 (s, 1H), HRMS exact mass of (M+Na)$^+$, 422.1170 amu; observed mass of (M+Na)$^+$, 422.1173 amu.

Example 2

General Synthetic Procedure for Δ2 CG Derivatives

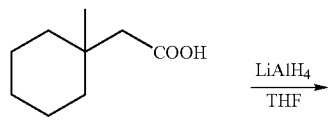

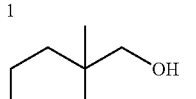

-continued

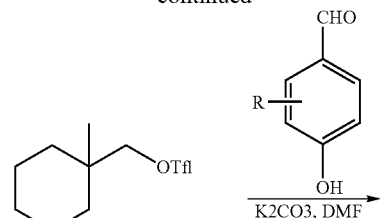

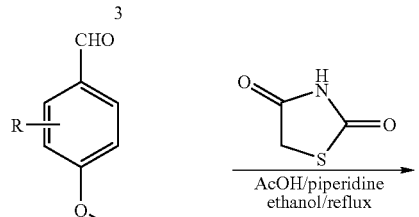

4 a-k

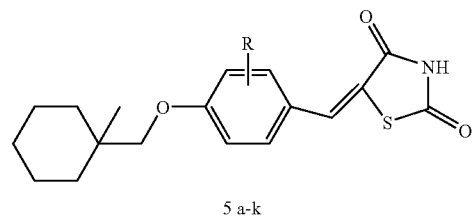

5 a-k

Example 3

General Synthetic Procedure for Δ2 TG Derivatives

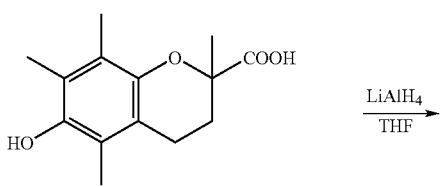

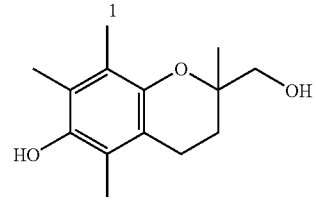

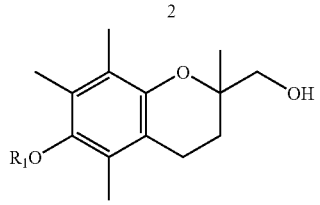

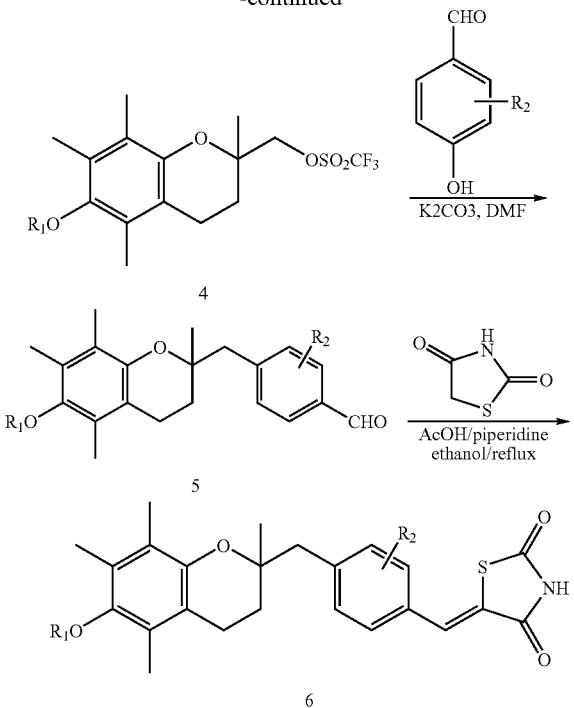

Example 4

General Synthetic Procedure for CG-OH Derivatives

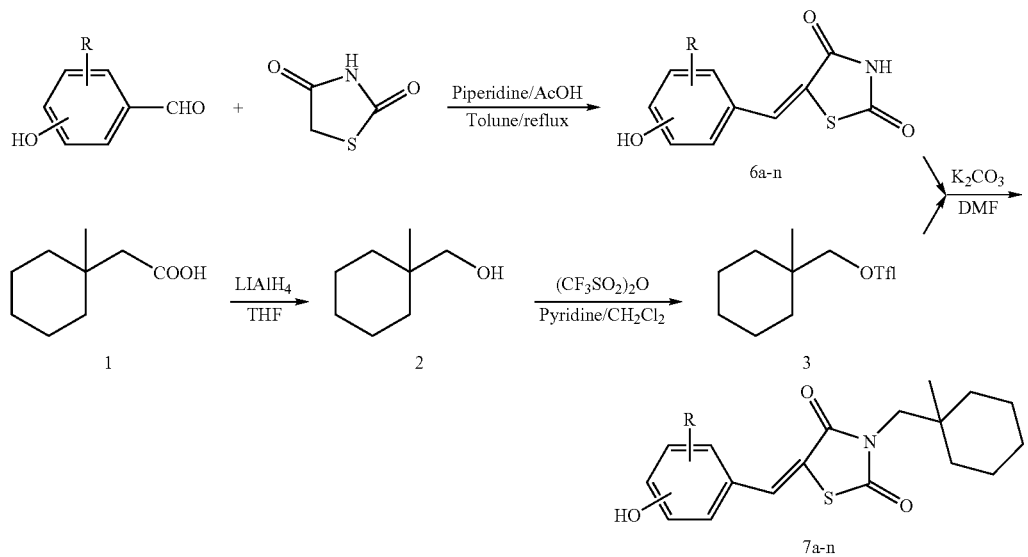

2-hydroxymethyl-2,5,7,8-tetramethyl-chroman-6-ol (2). 1.0 g of LiAlH$_4$ (26 mmol) was added in 100 mL of THF at 4° C. and stirred for half an hour, and then 5 g (20 mmol) of 6-hydroxy-2,5,7,8-tetramethylchroman-2-carboxylic acid (1) in 250 mL of THF was titrated dropwise over a period of 0.5 hour. The solution was reflux at room temperature overnight. After cooling to 4° C., 1 mL of H$_2$O, 1 mL of 1 N NaOH, and 2 mL of H$_2$O was slowly added to the solution to quench the reaction. The solution was stirred at room temperature for 2 more hours, filtered, and concentrated, giving the product 2 in 85% (0.45 mg) yield.

General Procedure for compound 3 (Ether): A solution of 2.0 mmol of 2-hydroxymethyl-2,5,7,8-tetramethyl-chroman-6-ol (2), 4.0 mmol of bromide and 5.0 mmol of K$_2$CO$_3$ in 20 mL of acetone was refluxed for 48 hrs. The solution was filtered and concentrated. The residue was re-suspended in ethyl acetate and purified by column chromatography.

General Procedure for compound 4 (Triflates): A solution of compound 3 (1 mmol) and 1.5 mmol pyridine in dry CH$_2$Cl$_2$ (5 mL) was stirred in ice bath, and 1.2 mmol triflate anhydride was added slowly to the solution. After 2 hr, the solution was concentrated and the residue was purified by column chromatography.

General Procedure for compound 5 (aldehydes): A mixture of compound 4 (0.5 mmol), benzaldehyde (0.6 mmol) and K$_2$CO$_3$ were dissolved in 3 mL DMF. The solution was heated to 60° C. overnight. After reaction, the solution was poured into water (10 ml), extracted with ethyl acetate (30 ml), washed with saturated saline and dried with anhydrous sodium sulfate. The solution was filtered and concentrated and the residue was purified by column chromatography.

General Procedure for Compound 6 (TG derivatives): A mixture of aldehyde 5 (0.3 mmol), 2,4-thiazolidinedione (0.4 mmol), catalytic amount of piperidine was refluxed in 5 mL EtOH for 24 h and then concentrated. The oil product was acidified with acetic acid and purified by chromatography and re-crystallization.

(1-methyl-cyclohexyl)-methanol (2). To a stirring solution of 0.27 g LiAlH$_4$ (20 mmol) in 10 mL of THF at 0° C. was added 1 g (7.0 mmol) of 1-methyl-cyclohexanecarboxylic acid in 50 mL of THF dropwise over a period of 1 hour. The solution was stirred at room temperature under N$_2$ for 6 hours. After 6 hours, 1 mL of H$_2$O, 1 mL of 1 N NaOH and 2 mL of H$_2$O was slowly added to the solution to quench the reaction. The solution was stirred at room temperature for another hour and then filtered out of solid. The solution was concentrated. Purification by flash silica gel chromatography (ethyl acetate/hexanes=1/2) gave the product in 71%.

Trifluoro-methanesulfonic acid 1-methyl-cyclohexylmethyl ester (3) A solution of compound 2 (1 mmol) in dry CH$_2$Cl$_2$ (5 mL) was cooled to 0° C. 1.1 mmol pyridine was added to the solution. 1.1 mmol triflate anhydride was added to the solution slowly to the solution. After 2 hr, the solution was concerned and the residue was purified by column chromatography. (ethyl acetate/hexanes=1/10).

General Procedure C for compounds 4a-k: A mixture of compound 3 (0.5 mmol), benzaldehyde (0.6 mmol) and K$_2$CO$_3$ were dissolved in 3 mL DMF. The solution was heated to 80° C. for 4 hr. the solution was poured into water, extracted with ethyl acetate (10 ml * 3), and concentrated. The residue was purified by chromatography.

General Procedure D for Delta2 Cg analogues (compounds 5a-k): A mixture of aldehydes (4a-k) (0.5 mmol), 2,4-thiazolidinedione, (0.6 mmol), catalytic amount of piperidine was refluxed in 5 mL EtOH for 24 h and then concentrated. The oil product was dissolved in ethyl acetate and poured into water and acidified with AcOH. The solution was extracted with ethyl acetate and concentrated. The residue was purified by chromatography.

General Procedure E for compounds 6a-m: A mixture of aldehydes (4a-k) (0.5 mmol), 2,4-thiazolidinedione, (0.6 mmol), catalytic amount of piperidine and acetic acid was refluxed in 5 mL Toluene for 24. The precipitated product was filtered, washed with 10 ml of toluene for three times and then dried in 60° C. vacuum oven overnight.

General Procedure C for compounds 7a-m: A mixture of compound 3 (0.5 mmol), compounds 6a-m (0.6 mmol) and K$_2$CO$_3$ (0.65 mmol) were stirred in 3 mL DMF. The solution was heated to 80° C. for 4 hr. the solution was poured into water, extracted with ethyl acetate (10 ml * 3), and concentrated. The residue was purified by chromatography.

Example 5

Analysis of AR-ablative Activity of Compounds

Cell Culture. LNCaP androgen-responsive (p53$^{+/+}$) and PC-3 androgen-nonresponsive (p53$^{-/-}$) prostate cancer cells were obtained from the American Type Culture Collection (Manassas, Va.), and were maintained in RPMI 1640 supplemented with 10% fetal bovine serum at 37° C. in a humidified incubator containing 5% carbon dioxide.

Cell Counting and Cell Viability Assay. LNCaP or PC-3 cells were placed in six-well plates (2.5×10$^5$ cells/well) in 10% FBS-supplemented RPMI 1640 for 24 h, and treated with various concentrations of compound 12 for additional 24, 48 and 72 h. Cells were then trypsinized and counted by using a Coulter counter (Model Z1 D/T, Beckman Coulter, Fullerton, Calif.). Cell viability was assessed by using the 3-(4,5-dimethylthiazol-2-yl)-2,5-diphenyl-2H-tetrazolium bromide (MTT) assay in six replicates in 96-well plates. LNCaP or PC-3 cells were seeded at 6000 cells per well in 10% FBS-supplemented RPMI 1640 for 24 h, followed by treatments with various compounds in 5% FBS-supplemented RPMI 1640 at the indicated concentrations. Controls received DMSO at a concentration equal to that in drug-treated cells. After the end of incubation, MTT (0.5 mg/ml) in 10% FBS-supplemented RPMI 1640 was added to each well, and cells were incubated at 37° C. for 2 hours. Medium was removed and the reduced MTT dye was solubilized in DMSO (200 μl/well). Absorbance was determined at 570 nm by a 96-well plate reader.

Transfection and Luciferase assay. The 3.6-kilobase AR promoter-linked reporter plasmid p-3600ARCAT was kindly provided by Dr. Chawnshang Chang (University of Rochester Medical Center, Rochester, N.Y.). The AR promoter gene (−3600 to +550) encompassing the transcription start site was isolated by using PCR to generate hAR-luc with suitable primers. The fragment was subcloned into the pGL3 luciferase reporter vector (Promega, Madison, Wis.) at KpnI and BglII in the multiple cloning site. The PPRE-x3-TK-Luc reporter vector contains three copies of the PPAR-response element (PPRE) upstream of the thymidine kinase promoter-luciferase fusion gene and was kindly provided by Dr. Bruce Spiegelman (Harvard University, Cambridge, Mass.). The pCMVSp1 plasmid was purchased from Origene Technologies, Inc. (Rockville, Md.). LNCaP or PC3 cells were transfected with 5 μg of individual plasmids in an Amaxa Nucleofector using a cell line-specific nucleofector kit according to the manufacturer's protocol (Amaxa Biosystems, Cologne, Germany), and then seeded in 6-well plates at 5×10$^5$ cells per well for 48 h. The transfection efficiency was determined to be 70-80% by transfecting cells with 2 μg of pmaxGFP plasmid, followed by fluorescence microscopy to measure GFP expression. For each transfection, herpes simplex virus thymidine kinase promoter-driven *Renilla reniformis* luciferase was used as an internal control for normalization.

For the reporter gene assay, after transfection, cells were cultured in 24-well plates in 10% FBS-supplemented RPMI 1640 medium for 48 h, subject to different treatments for the indicated times, collected, and lysed with passive lysis buffer (Promega). Fifty-μl aliquots of the lysates were added to 96-well plates, and luciferase activity was monitored after adding 100 μl of luciferase substrate (Promega) each well by using a MicroLumatPlus LB96V luminometer (Berthold Technologies, Oak Ridge, Tenn.) with the WinGlow software package. All transfection experiments were carried out in six replicate.

Cell Cycle Analysis. LNCaP cells were seeded in 6-well plates (2.5×10$^6$ cells/well) and treated with different concentrations of compound 12 for 72 h. After extensive washing with PBS, cells were trypsinized followed by fixation in ice-cold 80% ethanol at 4° C. overnight. Cells were then centrifuged for 5 min at 1500×g at room temperature, and stained with propidium iodide (50 μg/ml) and RNase A (100 units/ml) in PBS. Cell cycle phase distributions were determined on a FACScort flow cytometer and analyzed by the ModFitLT V3.0 program.

RT-PCR and Immunoblotting. LNCaP cells were cultured in T25 flasks at an initial density of 1×10$^6$ cells/flask. After exposure to various compounds at the indicated conditions, cells were subject to total RNA isolation by using an RNeasy mini-kit (QIAGEN, Valencia, Calif.). RNA concentrations were determined by measuring absorption at 260 nm in a spectrophotometer. Aliquots of 6 μg of total RNA from each sample were reverse-transcribed to cDNA using an Omniscript RT Kit (QIAGEN) according to the manufacturer's instructions, using suitable primers.

PCR reaction products were separated electrophoretically in 1.5% agarose gels. For immunoblotting, protein extracts were prepared by M-PER Mammalian Protein Extraction Reagent (Pierce, Rockford, Ill.) with freshly added 1% phosphatase and protease inhibitor cocktails (Calbiochem) followed by centrifugation at 13,000×g for 10 min. Supernatant was collected and protein concentration was determined by protein assay reagent (Bio-Rad, CA). Protein extracts were then suspended in 2×SDS sample buffer, and subject to 10% SDS-polyacrylamide gels. After electrophoresis, proteins were transferred to nitrocellulose membranes using a semidry transfer cell. The transblotted membrane was washed twice with Tris-buffered saline containing 0.1% Tween 20 (TBST). After blocking with TBST containing 5% nonfat milk for 1 h, the membrane was incubated with mouse monoclonal anti-AR (Santa Cruz) or anti-β-actin (MP Biomedicals) antibodies (diluted 1:1000) in 1% TBST nonfat milk at 4° C. overnight. After incubation with the primary antibody, the membrane was washed three times with TBST for a total of 30 min, followed by incubation with horseradish peroxidase conjugated goat anti-mouse IgG (diluted 1:2500) for 1 h at room temperature. After three thorough washes with TBST for a total of 30 min, the immunoblots were visualized by enhanced chemiluminescence.

Immunocytochemical Analysis. Cells were seeded onto coverslips in six-well plates ($2.5 \times 10^5$ cells/well) for 24 h followed by exposure to 5 μM compound 12 for an additional 48 h. After extensive washing with PBS, cells were fixed and permeabilized with PBS containing 0.1% Triton X-100 for 1 h, and then incubated with anti-AR (1:100 dilution) in PBS containing 0.1% Triton X-100, 0.2% bovine serum albumin, 0.5 mM PMSF, and 1 mM DTT at room temperature for 12 h followed by Alexa Fluor 488-conjugated goat anti-mouse IgG (1:100; Molecular Probes) for 2 h. Nuclear counterstaining was performed by mounting with 4,6-diamidino-2-phenylindole (DAPI)-containing medium. Images of immunocytochemically labeled samples were observed using a Nikon microscope (Eclipse TE300).

The invention claimed is:
1. A compound having the structure

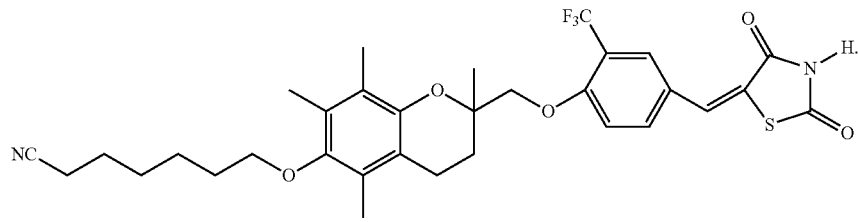

2. A compound selected from the group consisting of:
a. 5-[3-Bromo-4-(1-methyl-cyclohexylmethoxy)-benzylidene]-thiazolidine-2,4-dione

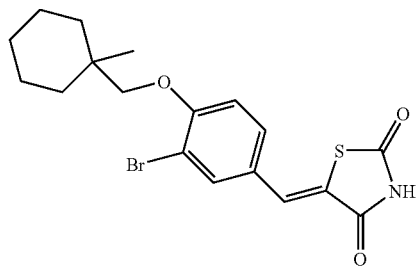

b. 5-[4-(1-Methyl-cyclohexylmethoxy)-3-nitro-benzylidene]-thiazolidine-2,4-dione

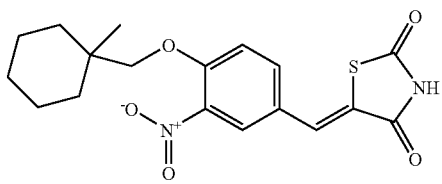

c. 5-[4-(1-Methyl-cyclohexylmethoxy)-3-trifluoromethyl-benzylidene]-thiazolidine-2,4-dione

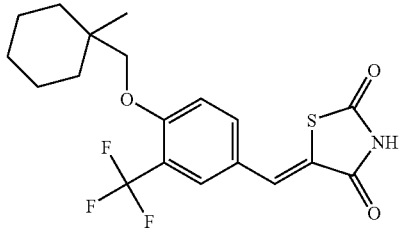

d. 5-[3-Methoxy-4-(1-methyl-cyclohexylmethoxy)-benzylidene]-thiazolidine-2,4-dione

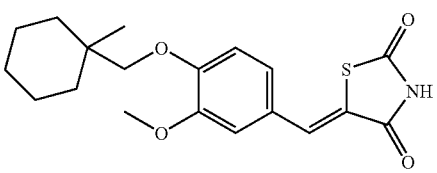

e. 5-[3-Ethoxy-4-(1-methyl-cyclohexylmethoxy)-benzylidene]-thiazolidine-2,4-dione

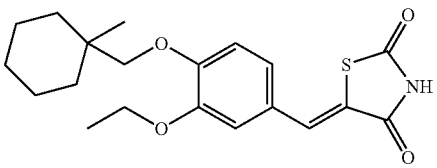

f. 5-[3,5-Dimethyl-4-(1-methyl-cyclohexylmethoxy)-benzylidene]-thiazolidine-2,4-dione

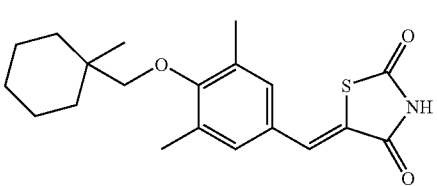

and g. 5-[4-(1-Methyl-cyclohexylmethoxy)-naphthalen-1-yl-methylene]-thiazolidine-2,4-dione

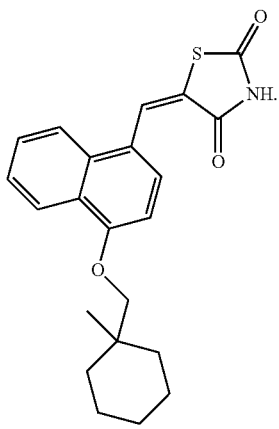

3. A compound of Formula IV:

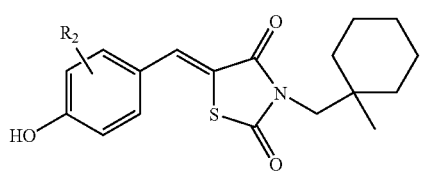

IV wherein $R_2$ is selected from the group consisting of hydrogen, halo, amino, methoxy, ethoxy, nitro, phenyl, di-alkyl, di-halo, trifluoromethyl, and hydroxyl.

4. A compound of claim 3, wherein the compound is selected from the group consisting of:

a. 5-(4-Hydroxy-benzylidene)-3-(1-methyl-cyclohexylmethyl)-thiazolidine-2,4-dione

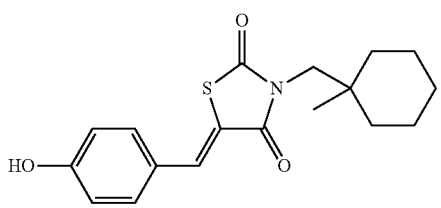

b. 5-(4-Hydroxy-3-trifluoromethyl-benzylidene)-3-(1-methyl-cyclohexylmethyl)-thiazolidine-2,4-dione

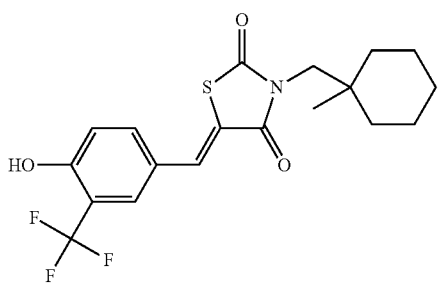

c. 5-(4-Hydroxy-3-nitro-benzylidene)-3-(1-methyl-cyclohexylmethyl)-thiazolidine-2,4-dione

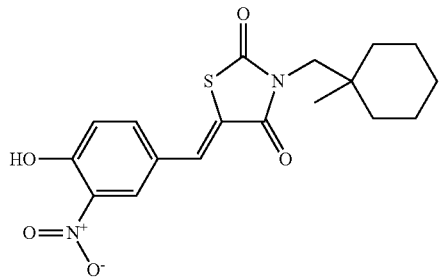

d. 5-(3-Bromo-4-hydroxy-benzylidene)-3-(1-methyl-cyclohexylmethyl)-thiazolidine-2,4-dione

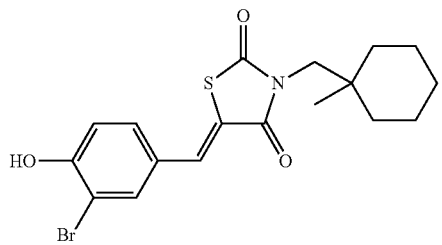

e. 5-(4-Hydroxy-3-methoxy-benzylidene)-3-(1-methyl-cyclohexylmethyl)-thiazolidine-2,4-dione

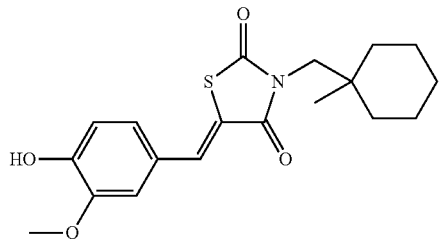

f. 5-(3,5-Dibromo-4-hydroxy-benzylidene)-3-(1-methyl-cyclohexylmethyl)-thiazolidine-2,4-dione

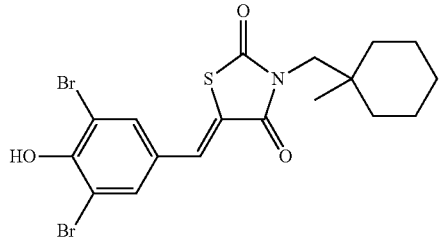

g. 5-(4-Hydroxy-3-iodo-5-methoxy-benzylidene)-3-(1-methyl-cyclohexylmethyl)-thiazolidine-2,4-dione

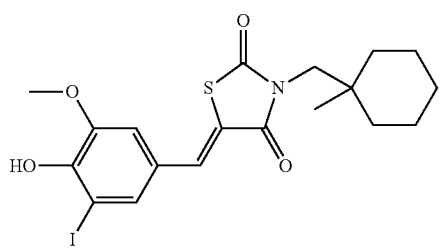

h. 5-(4-Hydroxy-3,5-dimethyl-benzylidene)-3-(1-methyl-cyclohexylmethyl)-thiazolidine-2,4-dione

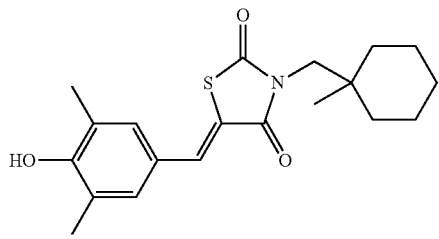

and i. 5-(4-Hydroxy-naphthalen-1-ylmethylene)-3-(1-methyl-cyclohexylmethyl)-thiazolidine-2,4-dione

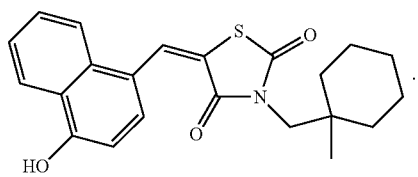

5. A compound of Formula V:

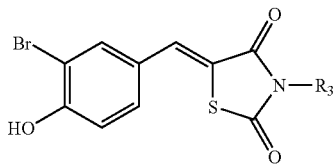

V wherein $R_3$ is selected from the group consisting of hydrogen, alkyl, cyclic alkyl, and arylmethoxy.

6. The compounds of claim 5, wherein the compounds are selected from the group consisting of:

a. 5-(3-Bromo-4-hydroxy-benzylidene)-3-ethyl-thiazolidine-2,4-dione

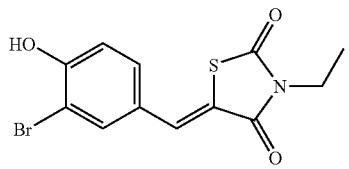

b. 5-(3-Bromo-4-hydroxy-benzylidene)-3-propyl-thiazolidine-2,4-dione

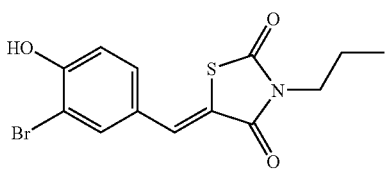

c. 5-(3-Bromo-4-hydroxy-benzylidene)-3-butyl-thiazolidine-2,4-dione

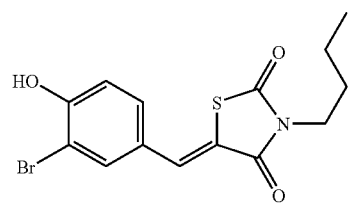

d. 5-(3-Bromo-4-hydroxy-benzylidene)-3-pentyl-thiazolidine-2,4-dione

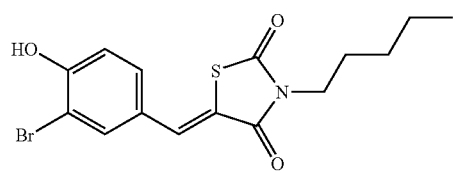

e. 5-(3-Bromo-4-hydroxy-benzylidene)-3-isopropyl-thiazolidine-2,4-dione

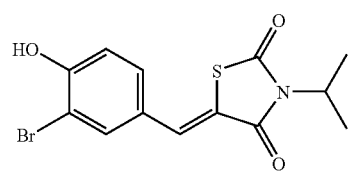

f. 5-(3-Bromo-4-hydroxy-benzylidene)-3-(4-methyl-pentyl)-thiazolidine-2,4-dione

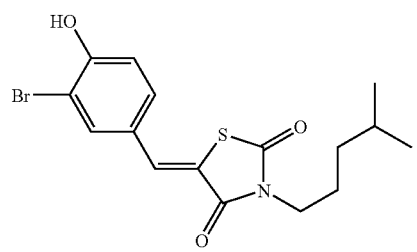

g. 5-(3-Bromo-4-hydroxy-benzylidene)-3-cyclohexylmethyl-thiazolidine-2,4-dione

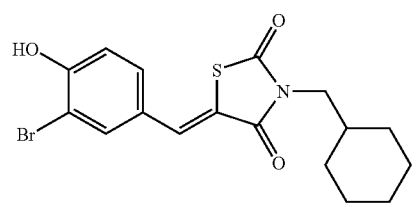

h. 3-Allyl-5-(3-bromo-4-hydroxy-benzylidene)-thiazolidine-2,4-dione

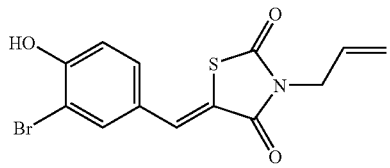

i. 5-(3-Bromo-4-hydroxy-benzylidene)-3-(3-methyl-but-2-enyl)-thiazolidine-2,4-dione

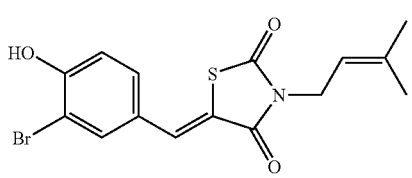

j. 3-Benzyl-5-(3-bromo-4-hydroxy-benzylidene)-thiazolidine-2,4-dione

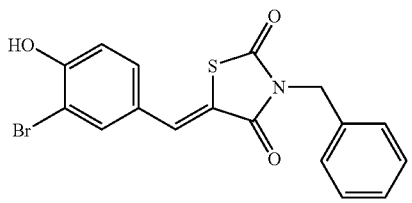

k. 4-[5-(3-Bromo-4-hydroxy-benzylidene)-2,4-dioxo-thiazolidin-3-ylmethyl]-benzonitrile

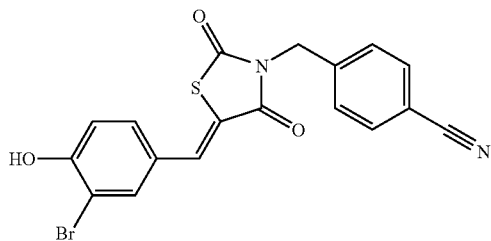

l. 4-[5-(3-Bromo-4-hydroxy-benzylidene)-2,4-dioxo-thiazolidin-3-yl]-butyronitrile

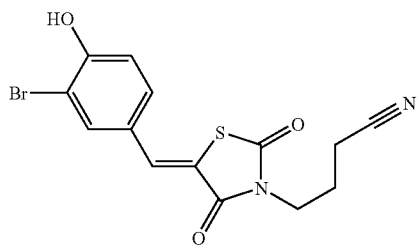

m. 4-[5-(3-Bromo-4-hydroxy-benzylidene)-2,4-dioxo-thiazolidin-3-yl]-butyric acid ethyl ester

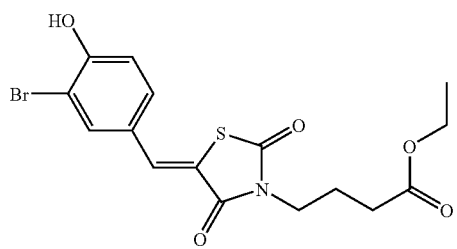

n. 6-[5-(3-Bromo-4-hydroxy-benzylidene)-2,4-dioxo-thiazolidin-3-yl]-2,2-dimethyl-hexanenitrile

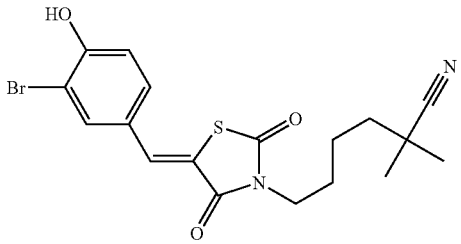

o. 5-(3-Bromo-4-hydroxy-benzylidene)-3-(tetrahydro-pyran-2-ylmethyl)-thiazolidine-2,4-dione

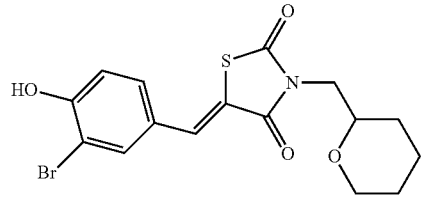

p. 5-(3-Bromo-4-hydroxy-benzylidene)-3-(6,6-dimethyl-[1,3]dioxan-4-ylmethyl)-thiazolidine-2,4-dione

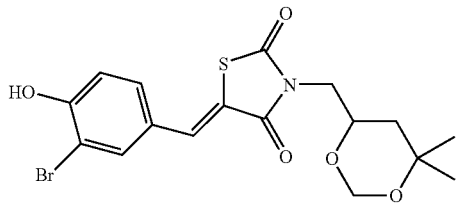

q. 5-(3-Bromo-4-hydroxy-benzylidene)-3-naphthalen-1-ylmethyl-thiazolidine-2,4-dione

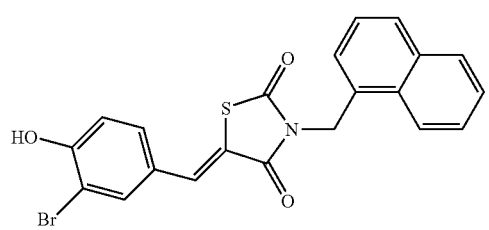

r. 5-(3-Bromo-4-hydroxy-benzylidene)-3-(3-chloro-5-fluoro-benzyl)-thiazolidine-2,4-dione

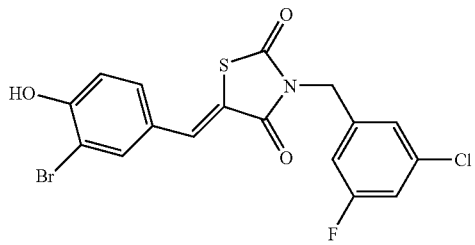

s. 5-(3-Bromo-4-hydroxy-benzylidene)-3-(2,3-dihydro-benzo[1,4]dioxin-2-ylmethyl)-thiazolidine-2,4-dione

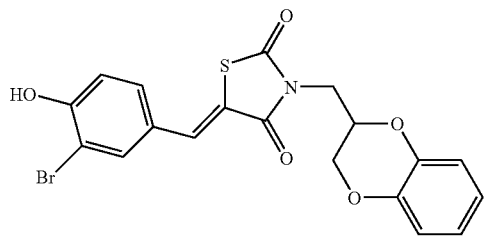

t. 3-(4-Benzoyl-benzyl)-5-(3-bromo-4-hydroxy-benzylidene)-thiazolidine-2,4-dione

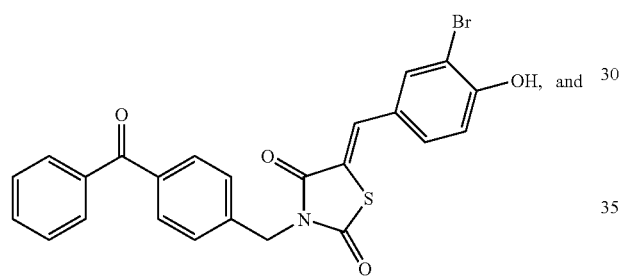

u. 4'-[5-(3-Bromo-4-hydroxy-benzylidene)-2,4-dioxo-thiazolidin-3-ylmethyl]-biphenyl-2-carbonitrile

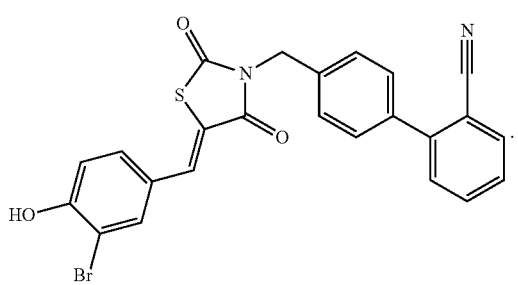

7. A compound of Formula VI:

VI

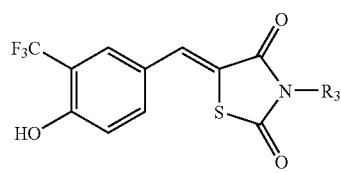

wherein $R_3$ is selected from the group consisting of hydrogen, alkyl, cyclic alkyl, and arylmethoxy.

8. The compounds of claim 7, wherein the compounds are selected from the group consisting of:

a. 5-(3-Trifluoromethyl-4-hydroxy-benzylidene)-3-ethyl-thiazolidine-2,4-dione

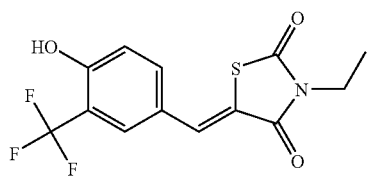

b. 5-(3-Trifluoromethyl-4-hydroxy-benzylidene)-3-propyl-thiazolidine-2,4-dione

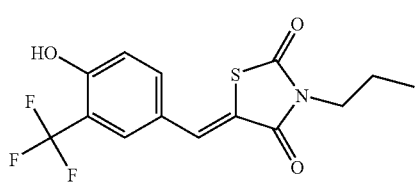

c. 5-(3-Trifluoromethyl-4-hydroxy-benzylidene)-3-butyl-thiazolidine-2,4-dione

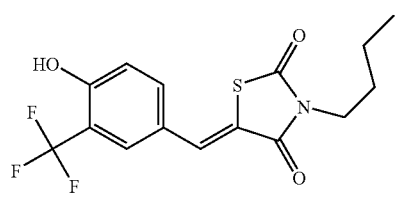

d. 5-(3-Trifluoromethyl-4-hydroxy-benzylidene)-3-pentyl-thiazolidine-2,4-dione

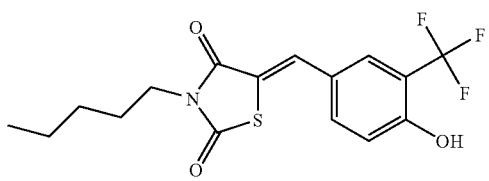

e. 5-(3-Trifluoromethyl-4-hydroxy-benzylidene)-3-isopropyl-thiazolidine-2,4-dione

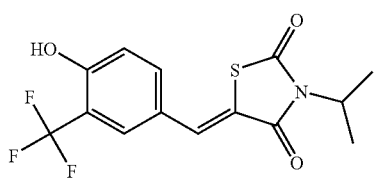

f. 5-(3-Trifluoromethyl-4-hydroxy-benzylidene)-3-(4-methyl-pentyl)-thiazolidine-2,4-dione

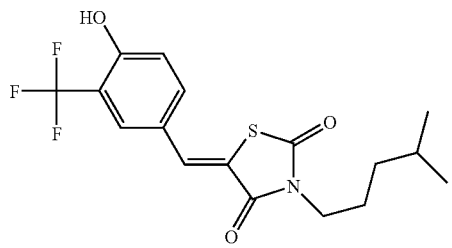

g. 5-(3-Trifluoromethyl-4-hydroxy-benzylidene)-3-cyclohexylmethyl-thiazolidine-2,4-dione

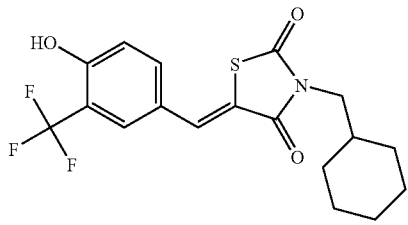

h. 3-Allyl-5-(3-Trifluoromethyl-4-hydroxy-benzylidene)-thiazolidine-2,4-dione

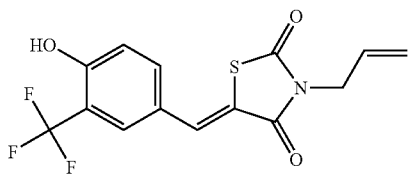

i. 5-(3-Trifluoromethyl-4-hydroxy-benzylidene)-3-(3-methyl-but-2-enyl)-thiazolidine-2,4-dione

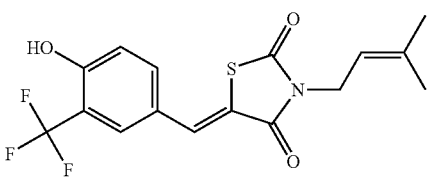

j. 3-Benzyl-5-(3-Trifluoromethyl-4-hydroxy-benzylidene)-thiazolidine-2,4-dione

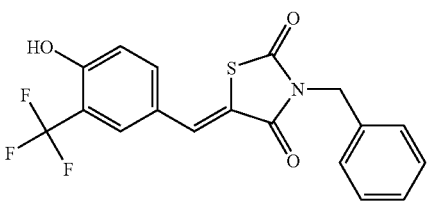

k. 4-[5-(3-Trifluoromethyl-4-hydroxy-benzylidene)-2,4-dioxo-thiazolidin-3-ylmethyl]-benzonitrile

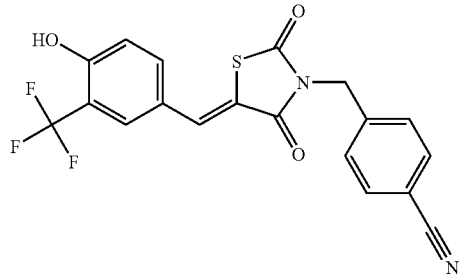

l. 4-[5-(3-Trifluoromethyl-4-hydroxy-benzylidene)-2,4-dioxo-thiazolidin-3-yl]-butyronitrile

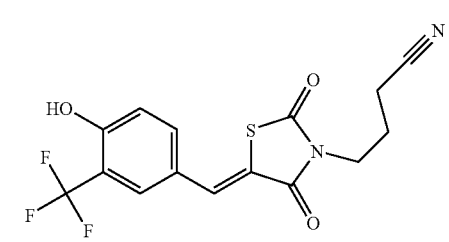

m. 4-[5-(3-Trifluoromethyl-4-hydroxy-benzylidene)-2,4-dioxo-thiazolidin-3-yl]-butyric acid ethyl ester

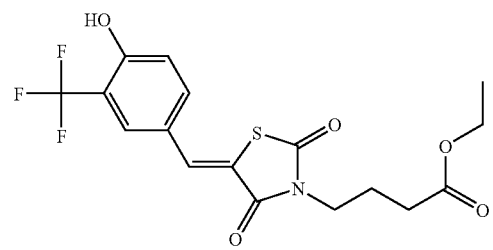

n. 6-[5-(3-Trifluoromethyl-4-hydroxy-benzylidene)-2,4-dioxo-thiazolidin-3-yl]-2,2-dimethyl-hexanenitrile

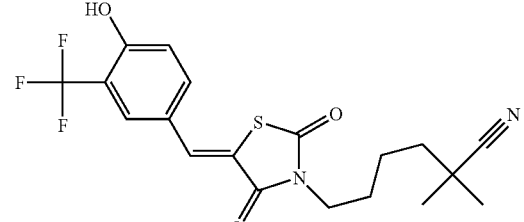

o. 5-(3-Trifluoromethyl-4-hydroxy-benzylidene)-3-(tetrahydro-pyran-2-ylmethyl)-thiazolidine-2,4-dione

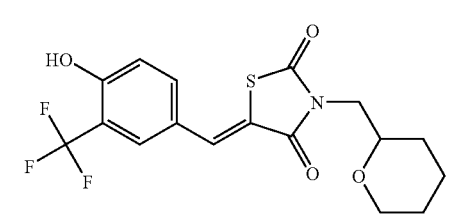

p. 5-(3-Trifluoromethyl-4-hydroxy-benzylidene)-3-(6,6-dimethyl-[1,3]dioxan-4-ylmethyl)-thiazolidine-2,4-dione

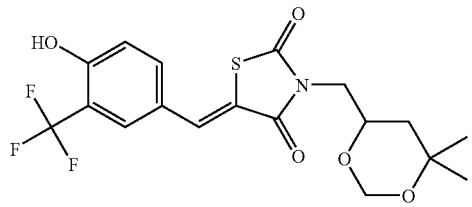

q. 5-(3-Trifluoromethyl-4-hydroxy-benzylidene)-3-naphthalen-1-ylmethyl-thiazolidine-2,4-dione

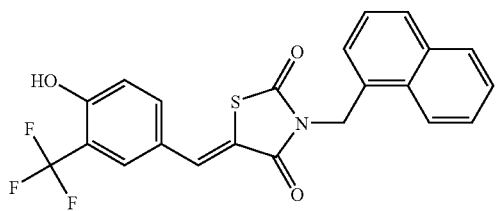

r. 5-(3-Trifluoromethyl-4-hydroxy-benzylidene)-3-(3-chloro-5-fluoro-benzyl)-thiazolidine-2,4-dione

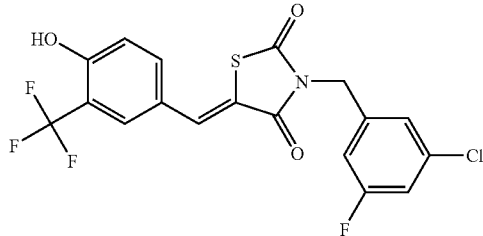

s. 5-(3-Trifluoromethyl-4-hydroxy-benzylidene)-3-(2,3-dihydro-benzo[1,4]dioxin-2-ylmethyl)-thiazolidine-2,4-dione

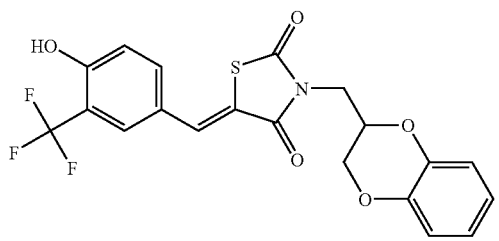

t. 3-(4-Benzoyl-benzyl)-5-(3-Trifluoromethyl-4-hydroxy-benzylidene)-thiazolidine-2,4-dione

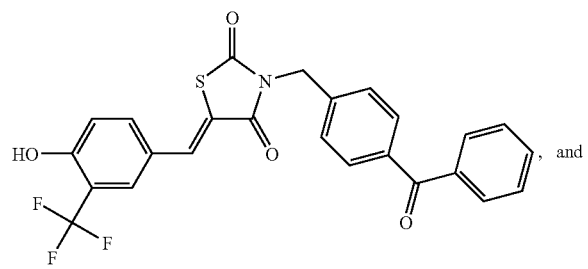

, and u. 4'-[5-(3-Trifluoromethyl-4-hydroxy-benzylidene)-2,4-dioxo-thiazolidin-3-ylmethyl]-biphenyl-2-carbonitrile

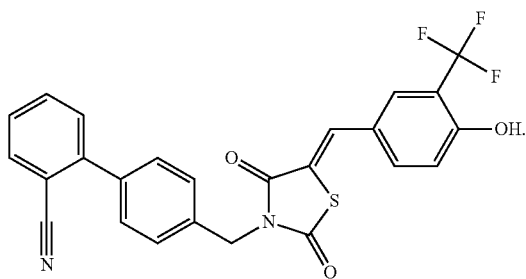

9. A compound selected from the group consisting of:

a. 5-(4-Fluoro-benzylidene)-3-(1-methyl-cyclohexylmethyl)-thiazolidine-2,4-dione

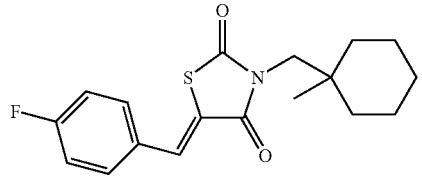

b. 5-(4-Chloro-benzylidene)-3-(1-methyl-cyclohexylmethyl)-thiazolidine-2,4-dione

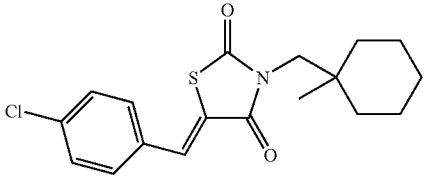

c. 5-(4-Bromo-benzylidene)-3-(1-methyl-cyclohexylmethyl)-thiazolidine-2,4-dione

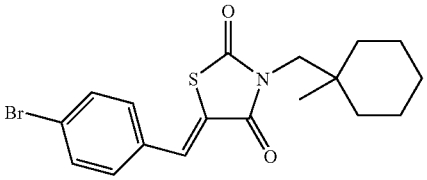

d. 3-(1-Methyl-cyclohexylmethyl)-5-(4-nitro-benzylidene)-thiazolidine-2,4-dione

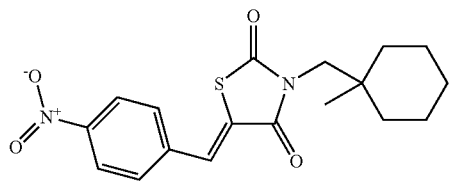

e. 3-(1-Methyl-cyclohexylmethyl)-5-(4-trifluoromethoxy-benzylidene)-thiazolidine-2,4-dione

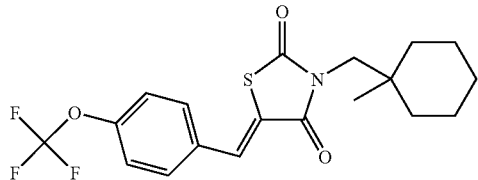

f. 5-(4-Diethylamino-benzylidene)-3-(1-methyl-cyclohexylmethyl)-thiazolidine-2,4-dione

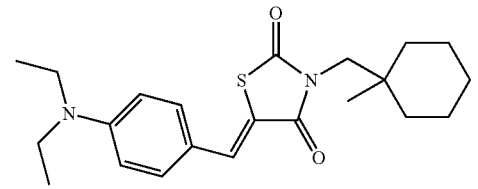

g. 5-(4-Dimethylamino-benzylidene)-3-(1-methyl-cyclohexylmethyl)-thiazolidine-2,4-dione

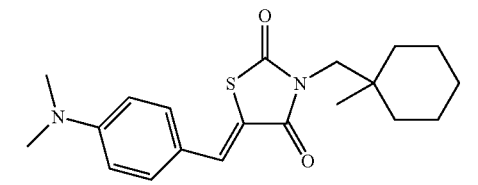

h. 5-(4-Hydroxymethyl-benzylidene)-3-(1-methyl-cyclohexylmethyl)-thiazolidine-2,4-dione

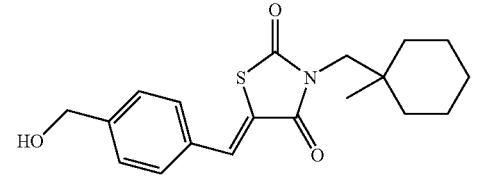

i. 4-[3-(1-Methyl-cyclohexylmethyl)-2,4-dioxo-thiazolidin-5-ylidenemethyl]-benzonitrile

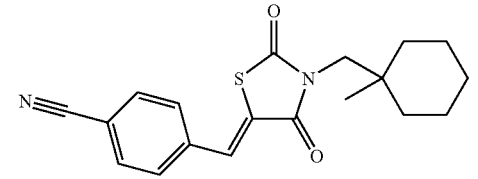

j. 4-[3-(1-Methyl-cyclohexylmethyl)-2,4-dioxo-thiazolidin-5-ylidenemethyl]-benzaldehyde

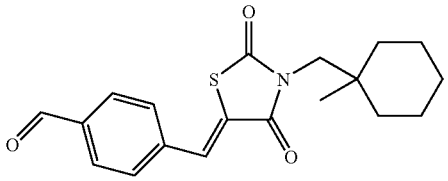

k. 4-[3-(1-Methyl-cyclohexylmethyl)-2,4-dioxo-thiazolidin-5-ylidenemethyl]-benzoic acid methyl ester

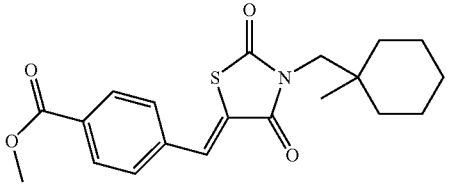

l. 4-[3-(1-Methyl-cyclohexylmethyl)-2,4-dioxo-thiazolidin-5-ylidenemethyl]-benzoic acid

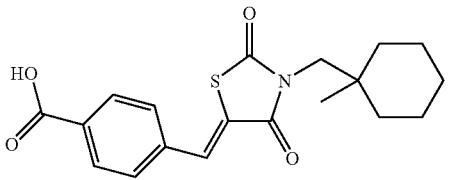

m. N-{4-[3-(1-Methyl-cyclohexylmethyl)-2,4-dioxo-thiazolidin-5-ylidenemethyl]-phenyl}-acetamide

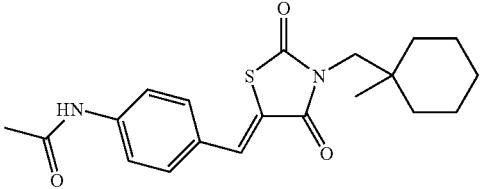

n. N-{4-[3-(1-Methyl-cyclohexylmethyl)-2,4-dioxo-thiazolidin-5-ylidenemethyl]-phenyl}-propionamide

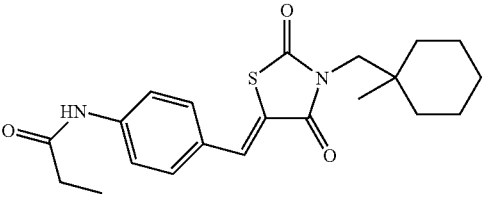

o. Hexadecanoic acid {4-[3-(1-methyl-cyclohexylmethyl)-2,4-dioxo-thiazolidin-5-ylidenemethyl]-phenyl}-amide

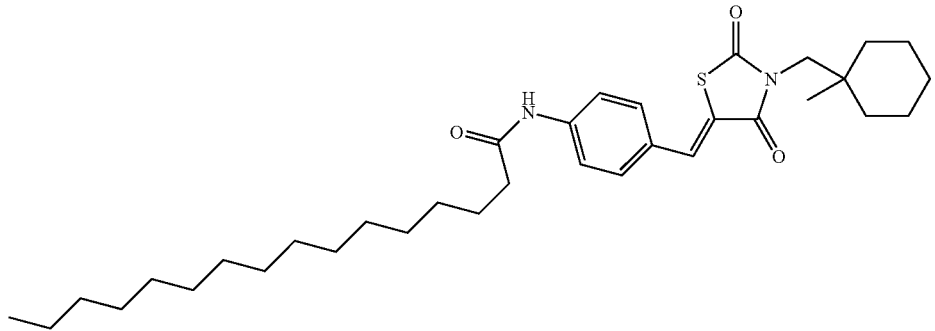

p. Cyclohexanecarboxylic acid {4-[3-(1-methyl-cyclohexylmethyl)-2,4-dioxo-thiazolidin-5-ylidenemethyl]-phenyl}-amide

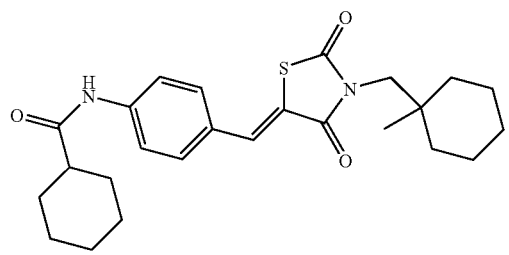

q. 2,2,2-Trichloro-N-{4-[3-(1-methyl-cyclohexylmethyl)-2,4-dioxo-thiazolidin-5-ylidenemethyl]-phenyl}-acetamide

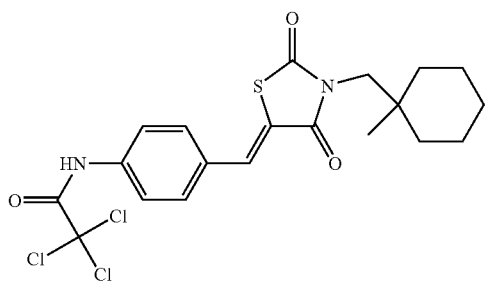

r. N-{4-[3-(1-Methyl-cyclohexylmethyl)-2,4-dioxo-thiazolidin-5-ylidenemethyl]-phenyl}-benzamide

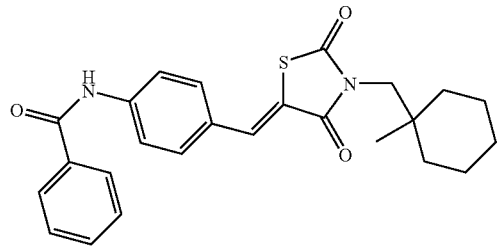

s. N-{4-[3-(1-Methyl-cyclohexylmethyl)-2,4-dioxo-thiazolidin-5-ylidenemethyl]-phenyl}-methanesulfonamide

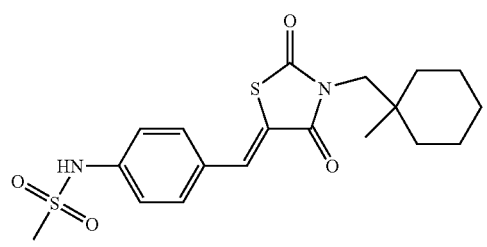

t. N-{4-[3-(1-Methyl-cyclohexylmethyl)-2,4-dioxo-thiazolidin-5-ylidenemethyl]-phenyl}-2-nitro-benzenesulfonamide

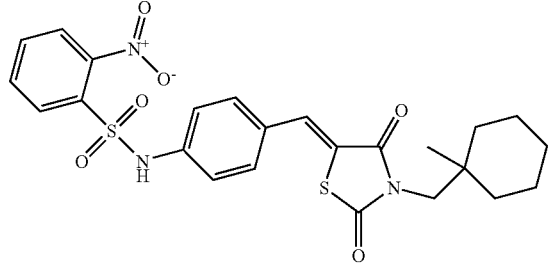

u. N-(4-{4-[3-(1-Methyl-cyclohexylmethyl)-2,4-dioxo-thiazolidin-5-ylidenemethyl]-phenylsulfamoyl}-phenyl)-acetamide

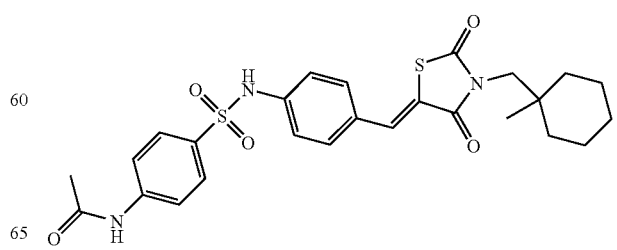

v. 4-Methyl-N-{4-[3-(1-methyl-cyclohexylmethyl)-2,4-dioxo-thiazolidin-5-ylidenemethyl]-phenyl}-benzenesulfonamide

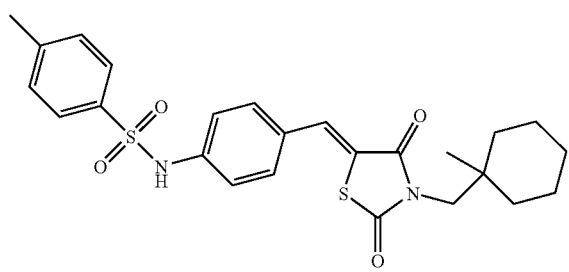

w. 4-Chloro-N-{4-[3-(1-methyl-cyclohexylmethyl)-2,4-dioxo-thiazolidin-5-ylidenemethyl]-phenyl}-benzenesulfonamide

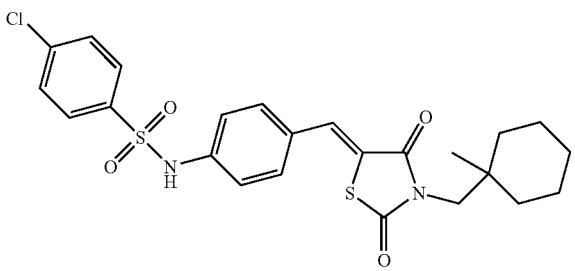

x. 4-(Z)-Acetyl-N-{4-[3-(1-methyl-cyclohexylmethyl)-2,4-dioxo-thiazolidin-5-ylidenemethyl]-phenyl}-benzenesulfonamide

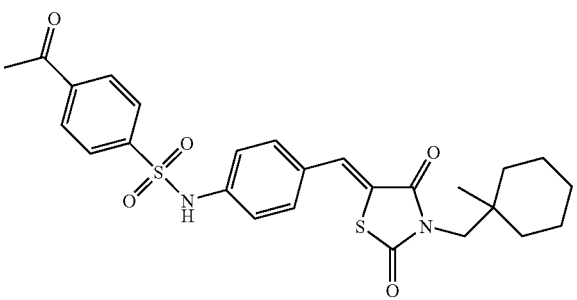

y. N-{4-[3-(1-Methyl-cyclohexylmethyl)-2,4-dioxo-thiazolidin-5-ylidenemethyl]-phenyl}-4-nitro-benzenesulfonamide

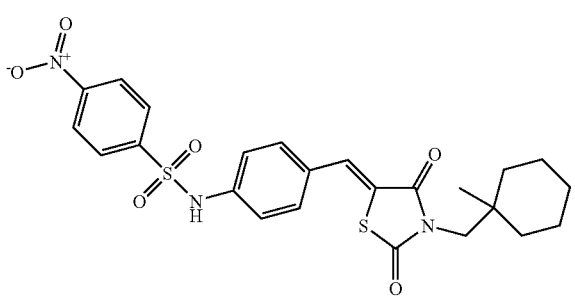

z. N-{4-[3-(1-Methyl-cyclohexylmethyl)-2,4-dioxo-thiazolidin-5-ylidenemethyl]-phenyl}-4-nitro-3-trifluoromethyl-benzenesulfonamide

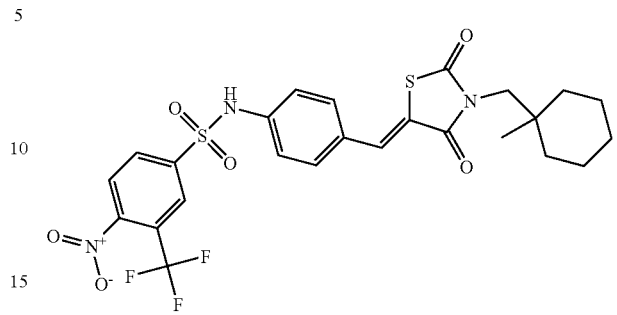

aa. 4-Chloro-N-{4-[3-(1-methyl-cyclohexylmethyl)-2,4-dioxo-thiazolidin-5-ylidenemethyl]-phenyl}-3-nitro-benzenesulfonamide

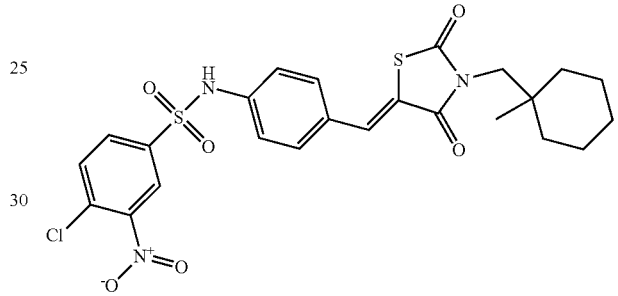

ab. 2-Methoxy-N-{4-[3-(1-methyl-cyclohexylmethyl)-2,4-dioxo-thiazolidin-5-ylidenemethyl]-phenyl}-4-nitro-benzenesulfonamide

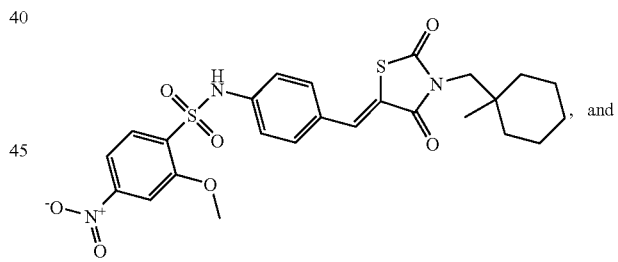, and ac. 3,4-Dimethoxy-N-{4-[3-(1-methyl-cyclohexylmethyl)-2,4-dioxo-thiazolidin-5-ylidenemethyl]-phenyl}-benzenesulfonamide

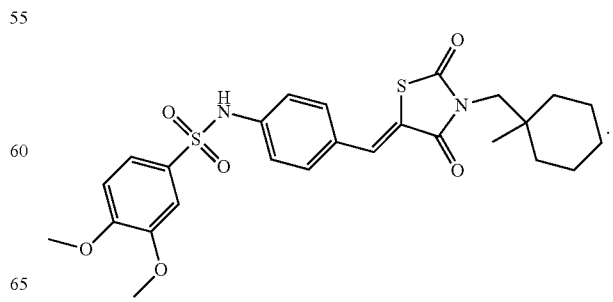.

10. A method of treating, inhibiting, or delaying the onset of prostate cancer in a subject in need of treatment, the method comprising administering a therapeutically effective amount of a compound of Formula I:

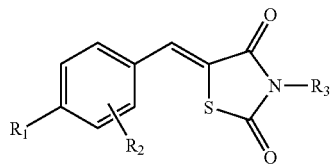

I wherein R₁ is selected from the group consisting of hydroxyl, amino, halo, hydroxyalkyl, alkylmethoxy, cycloalkylmethoxy, arylmethoxy, NHCOR, NHSO₂R, and CH₂R;

wherein R₂ is selected from the group consisting of hydrogen, halo, amino, methoxy, ethoxy, nitro, phenyl, di-alkyl, di-halo, trifluoromethyl, and hydroxyl;

wherein R₃ is selected from the group consisting of hydrogen, alkyl, cyclic alkyl, and arylmethoxy;

or a pharmaceutically-acceptable salt thereof, to the subject in need of such treatment.

11. The method of claim 10, wherein the prostate cancer is hormone-refractory prostate cancer (HRPC).

12. The method of claim 10, wherein R₁ is a hydroxyl moiety and R₃ is a 1-methyl-cyclohexylmethyl moiety.

13. The method of claim 12, wherein the compound is selected from the group consisting of:

a. 5-(4-Hydroxy-benzylidene)-3-(1-methyl-cyclohexylmethyl)-thiazolidine-2,4-dione

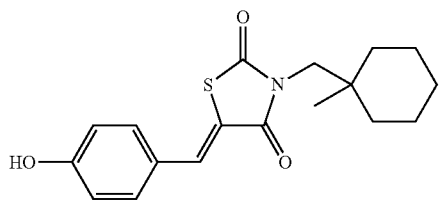

b. 5-(4-Hydroxy-3-trifluoromethyl-benzylidene)-3-(1-methyl-cyclohexylmethyl)-thiazolidine-2,4-dione

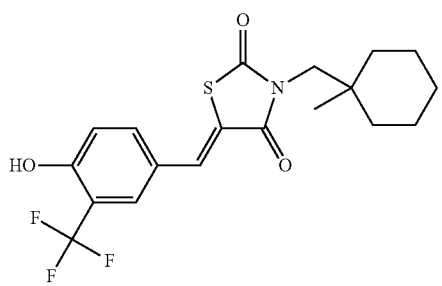

c. 5-(4-Hydroxy-3-nitro-benzylidene)-3-(1-methyl-cyclohexylmethyl)-thiazolidine-2,4-dione

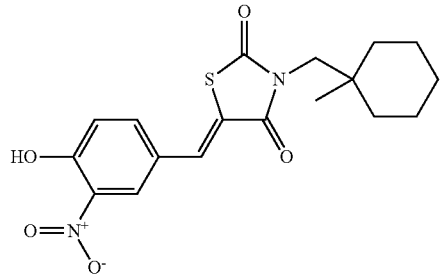

d. 5-(3-Bromo-4-hydroxy-benzylidene)-3-(1-methyl-cyclohexylmethyl)-thiazolidine-2,4-dione

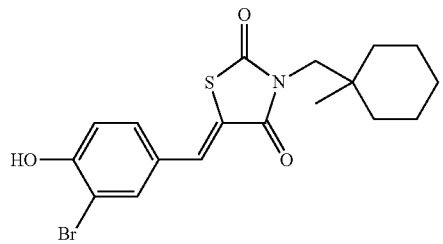

e. 5-(4-Hydroxy-3-methoxy-benzylidene)-3-(1-methyl-cyclohexylmethyl)-thiazolidine-2,4-dione

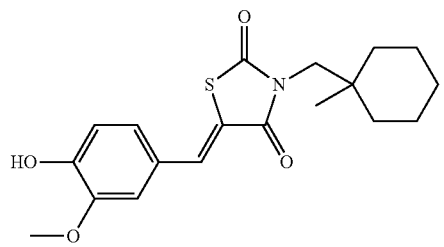

f. 5-(3,5-Dibromo-4-hydroxy-benzylidene)-3-(1-methyl-cyclohexylmethyl)-thiazolidine-2,4-dione

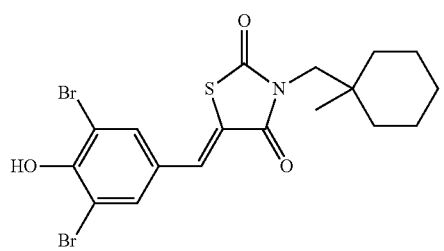

g. 5-(4-Hydroxy-3-iodo-5-methoxy-benzylidene)-3-(1-methyl-cyclohexylmethyl)-thiazolidine-2,4-dione

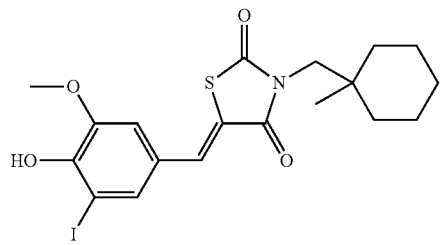

h. 5-(4-Hydroxy-3,5-dimethyl-benzylidene)-3-(1-methyl-cyclohexylmethyl)-thiazolidine-2,4-dione
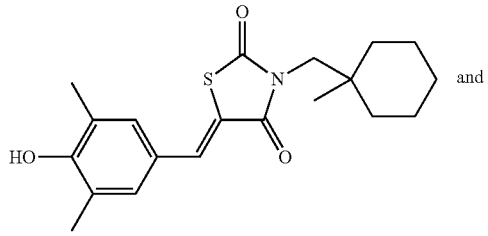
and
i. 5-(4-Hydroxy-naphthalen-1-ylmethylene)-3-(1-methyl-cyclohexylmethyl)-thiazolidine-2,4-dione
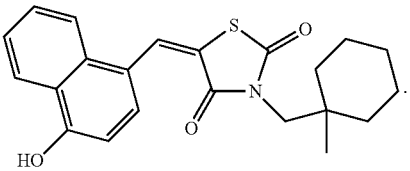
* * * * *

UNITED STATES PATENT AND TRADEMARK OFFICE
CERTIFICATE OF CORRECTION

PATENT NO. : 7,973,062 B2  
APPLICATION NO. : 12/389759  
DATED : July 5, 2011  
INVENTOR(S) : Ching-Shih Chen, Dasheng Wang and Jian Yang Page 1 of 1

It is certified that error appears in the above-identified patent and that said Letters Patent is hereby corrected as shown below:

In the Specification

At Column 1, Lines 11-15 should read:
This invention was made with government support under grant numbers CA094829 and CA112250 awarded by the National Institutes of Health and grant number W81XWH-05-1-0089 awarded by the United States Army Medical Research and Materiel Command. The government has certain rights in the invention.

Signed and Sealed this  
Twenty-eighth Day of July, 2020

Andrei Iancu  
*Director of the United States Patent and Trademark Office*